(12) United States Patent
Cooper et al.

(10) Patent No.: US 10,345,213 B2
(45) Date of Patent: Jul. 9, 2019

(54) PARTICLE DETECTION SYSTEM AND RELATED METHODS

(71) Applicant: Xtralis Technologies Ltd, Nassau, NP (BS)

(72) Inventors: Kate Cooper, Caulfield North (AU); Ronald Knox, Mount Eliza (AU)

(73) Assignee: Garrett Thermal Systems Limited, Berkshire (GB)

(*) Notice: Subject to any disclaimer, the term of this patent is extended or adjusted under 35 U.S.C. 154(b) by 0 days.

(21) Appl. No.: 14/895,450

(22) PCT Filed: Jun. 3, 2014

(86) PCT No.: PCT/AU2014/050060
§ 371 (c)(1),
(2) Date: Dec. 2, 2015

(87) PCT Pub. No.: WO2014/194379
PCT Pub. Date: Dec. 11, 2014

(65) Prior Publication Data
US 2016/0116389 A1 Apr. 28, 2016

(30) Foreign Application Priority Data

Jun. 3, 2013 (AU) ................................ 2013901993
Jul. 11, 2013 (AU) ................................ 2013902569
Jan. 6, 2014 (AU) ................................ 2014900028

(51) Int. Cl.
*G01N 15/00* (2006.01)
*G01N 17/00* (2006.01)
(Continued)

(52) U.S. Cl.
CPC ..... *G01N 15/0205* (2013.01); *G01N 15/0227* (2013.01); *G01N 15/0266* (2013.01);
(Continued)

(58) Field of Classification Search
None
See application file for complete search history.

(56) References Cited

U.S. PATENT DOCUMENTS 3,958,122 A * 5/1976 Jowett ................. G01M 15/108
250/344
3,995,960 A * 12/1976 Fletcher ............. G01N 21/1702
250/343
(Continued)

FOREIGN PATENT DOCUMENTS

AU 2011201151 4/2011
EP 1868173 A2 12/2007
(Continued)

OTHER PUBLICATIONS

"International Application No. PCT/AU2014/050060, International Search Report and Written Opinion dated Aug. 25, 2014", (Aug. 25, 2014), 14 pgs.
(Continued)

*Primary Examiner* — Shawn Decenzo
*Assistant Examiner* — Jarreas C Underwood
(74) *Attorney, Agent, or Firm* — Schwegman Lundberg & Woessner, P.A.

(57) ABSTRACT

A particle detector, e.g. a smoke detector is described. In one form the detector includes a detection chamber and radiation source emitting a single beam of radiation. The detector also includes a radiation receiving system and an imaging system arranged to receive radiation from a common region of interest. Methods and systems for analyzing the output of a particle detector are also disclosed.

27 Claims, 13 Drawing Sheets

(51) Int. Cl.
*G01N 15/02* (2006.01)
*G08B 17/10* (2006.01)
*G08B 17/113* (2006.01)
G01N 15/14 (2006.01)
G01N 35/00 (2006.01)

(52) U.S. Cl.
CPC ............ *G08B 17/10* (2013.01); *G08B 17/113* (2013.01); *G01N 15/1404* (2013.01); *G01N 15/1436* (2013.01); *G01N 15/1463* (2013.01); *G01N 2015/0046* (2013.01); *G01N 2015/0238* (2013.01); *G01N 2035/00881* (2013.01)

(56) References Cited

U.S. PATENT DOCUMENTS

| | | | | |
|---|---|---|---|---|
| 4,245,909 A * | 1/1981 | Loos | ............... | G01N 15/0211 250/574 |
| 4,441,816 A * | 4/1984 | Hencken | ........... | G01N 15/0205 356/335 |
| 4,679,939 A * | 7/1987 | Curry | ................ | G01N 15/0205 356/336 |
| 4,999,513 A * | 3/1991 | Ito | ................. | G01N 15/147 250/575 |
| 5,166,789 A * | 11/1992 | Myrick | ................... | G01V 9/00 348/144 |
| 5,373,160 A * | 12/1994 | Taylor | ................... | G01N 21/39 250/338.5 |
| 5,451,931 A | 9/1995 | Muller et al. | | |
| 6,055,052 A * | 4/2000 | Lilienfeld | ............. | G01N 15/02 250/574 |
| 6,078,040 A | 6/2000 | Endo | | |
| 6,184,537 B1 * | 2/2001 | Knox | .................. | G01N 21/53 250/574 |
| 6,198,110 B1 * | 3/2001 | Kaye | ................ | G01N 15/1436 250/573 |
| 6,285,291 B1 * | 9/2001 | Knox | ................... | G08B 17/10 340/521 |
| 6,519,033 B1 * | 2/2003 | Quist | ................. | G01N 15/14 356/337 |
| 7,250,871 B2 | 7/2007 | Williams et al. | | |
| 7,983,445 B2 * | 7/2011 | Knox | ................... | G01N 21/53 382/103 |
| 7,990,525 B2 * | 8/2011 | Kanda | ................... | G01N 21/51 356/73 |
| 8,289,178 B2 * | 10/2012 | Slemon | ................ | G08B 17/107 250/216 |
| 9,013,692 B2 * | 4/2015 | Hu | ....................... | G01N 15/147 250/459.1 |
| 9,851,291 B2 * | 12/2017 | Silcott | ............... | G01N 15/1434 |
| 2002/0105645 A1 * | 8/2002 | Eriksson | ........... | G01N 15/0227 356/335 |
| 2005/0225745 A1 * | 10/2005 | Nagai | ................ | G01N 15/147 356/73 |
| 2007/0024459 A1 | 2/2007 | Cole | | |
| 2008/0221711 A1 * | 9/2008 | Trainer | .............. | G01N 15/0205 700/54 |
| 2012/0127298 A1 * | 5/2012 | Sieracki | ................ | G01N 21/05 348/79 |

FOREIGN PATENT DOCUMENTS

| | | |
|---|---|---|
| JP | S6151569 U | 3/1986 |
| JP | 2000292340 | 10/2000 |
| JP | 2001296232 | 10/2001 |
| JP | 2003065941 A | 3/2003 |
| JP | 2008008911 A | 1/2008 |
| JP | 2008519965 A | 6/2008 |
| JP | 2009002751 A | 1/2009 |
| JP | 2011503581 | 1/2011 |
| JP | 2013083656 A | 5/2013 |
| WO | WO-2007/095675 A1 | 8/2007 |
| WO | WO-2011/106850 | 9/2011 |
| WO | WO-2014/194379 | 12/2014 |

OTHER PUBLICATIONS

"Chinese Application Serial No. 201480031757.5, Office Action dated Nov. 11, 2016", (W/ English Translation), 25 pgs.
"European Application Serial No. 14806808.3, extended European Search Report dated Feb. 6, 2017", 9 pgs.
"Japanese Application No. 2016-515576, Notification of Reasons for Refusal dated Apr. 24, 2018", (Apr. 24, 2018), 7 pgs.

* cited by examiner $$S = \sum I - \tfrac{1}{2}\left(\sum B_1 + B_2\right)$$

PARTICLE DETECTION SYSTEM AND RELATED METHODS

PRIORITY CLAIM TO RELATED APPLICATIONS

This application is a U.S. national stage application filed under 35 U.S.C. § 371 from International Application Serial No. PCT/AU2014/050060, which was filed 3 Jun. 2014, and published as WO2014/194379 on 11 Dec. 2014, and which claims priority to Australia Application No. 2013901993, filed 3 Jun. 2013, and claims priority to Australia Application No. 2013902569, filed 11 Jul. 2013, and claims priority to Australia Application No. 2014900028, filed 6 Jan. 2014, which applications and publication are incorporated by reference as if reproduced herein and made a part hereof in their entirety, and the benefit of priority of each of which is claimed herein.

FIELD OF THE INVENTION

The present invention relates to particle detection systems and methods, and analysis of the particle detection events in particle detection systems. Preferred embodiments relate to aspirated smoke detection systems.

BACKGROUND OF THE INVENTION

Aspirated smoke detection (ASD) systems are widely deployed, most commonly, in situations where high sensitivity particle detection is needed to protect valuable systems and infrastructure; and lives. ASD systems typically comprise a particle detector coupled to an air sampling system that delivers an air sample from a location being monitored to the particle detection system. These aspirated smoke detection systems have the dual requirement of high sensitivity and high reliability which present certain engineering challenges.

High sensitivity detection requires that the particle detection system remains accurately calibrated and free from soiling by dust and debris throughout its life. Moreover, it is also preferable that the system has some mechanism to avoid false alarms caused by nuisance and particles which do not indicate the presence of fire. To some extent both ends can be achieved by the use of filters which seek to remove any dust from the sample air so that only smoke particles remain. However, this is not necessarily an easy task as dust particles and smoke particles have size distributions which overlap. Also over time, filters clog and their filtration characteristics may change. This leads to a need to change filters as part of a maintenance schedule. Furthermore the dirtying of the detection chamber of the particle detection system over time as particles settle within the chamber also degrades system performance and impacts reliability. In particular, dirtying of the chamber causes an increase in background radiation within the detection chamber, which effectively adds noise to any detection signal produced and may increase background radiation level to the alarm threshold level in extreme cases.

Accordingly, there is a need for particle detection systems, particularly in the field of aspirating smoke detection systems which better handle the real world situations in which they are used, such that they can maintain detection accuracy, high sensitivity and trouble free operation over long periods.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect there is disclosed a particle detector, preferably being a smoke detector, the particle detector including:
  a detection chamber for receiving a sample flow for analysis;
  a radiation source configured to emit a beam of radiation having known polarisation characteristics, said beam propagating across at least part of the chamber and being arranged to traverse the sample flow at a region of interest;
  a radiation receiving system configured to receive radiation that is scattered from the beam by interaction with particles entrained in the sample flow, said radiation receiving system being further configured to receive radiation at a plurality of scattering angles and in a plurality of polarisation angles with respect to a direction of propagation and known polarisation of the beam, and generate at least one output signal representing the received radiation;
  a controller configured to analyse the at least one output signal representing the received radiation to determine the presence of particles entrained in the sample flow.

Most preferably the radiation source includes an optical system to focus the beam. Preferably the beam is focused so that it converges towards the region of interest.

Preferably the radiation receiving system includes a plurality of radiation receiving sensors each configured to receive radiation at a respective scattering angle. Each sensor is preferably arranged to receive radiation at a known polarisation angle relative to the angle of polarisation to the beam. Preferably the radiation receiving system includes a first plurality of radiation receiving sensors configured to receive radiation a first polarisation angle relative to the beam, wherein each of said first plurality of radiation sensors are arranged to receive at a respective scattering angle. Most preferably the radiation receiving system includes a second plurality of radiation receiving sensors configured to receive radiation a second polarisation angle (different to the first polarisation angle) relative to the beam, wherein said second plurality of radiation sensors are each arranged to receive radiation at a respective scattering angle.

Preferably the first and second plurality of radiation sensors are arranged such that at least one of the sensors of each of the first and second plurality of radiation sensors are arranged to receive radiation at the same respective scattering angle.

Each radiation sensor is preferably configured to provide an output signal representing a respective received radiation level. In a preferred embodiment the detector can be configured to temporally correlate the output signals from at least a subset of the sensors. The temporally correlated output signals can preferably be used to identify an interaction between a particle of interest and the beam. Most preferably the temporally correlated output signals are used to determine a particle characteristic, such as particle size or colour.

In a some embodiments one or more of, sample flow rate; beam cross section; shape; or alignment, relative to either or both of sensors comprising the radiation sensing system; are selected or controlled, such that for a predetermined concentration of particles in the sample flow, on average, interactions between particles entrained in the sample and the beam, that scatter radiation in a manner that may be received directly by a sensor of the radiation sensing system, are substantially non-overlapping. In this way individual particles may be detected.

Sample flow rate can be controlled by controlling the rate at which air is drawn through the system (e.g. by controlling fan speed). Alternatively or in combination, the flow rate through a sub-flowpath that leads to the detection chamber is controlled (e.g. by controlling a fan in that flow path or changing the flow path impedance, say be opening or closing a valve or the like). For each particle of interest so detected, a particle size or total brightness can be determined. Data relating to particle size or total brightness for multiple particle detection events can be stored. The stored particle size or total apparent particle brightness data is preferably used to determine a particle size or total apparent particle brightness distribution in the sample flow. The determined particle size or total apparent particle brightness distribution can be used to determine whether the particles detected represent particles of interest (e.g. smoke particles) or nuisance particles (e.g. dust) or a mixture of both. In the event that it is determined that particles of interest are determined an action can be taken, e.g. changing an alarm status or sending an alarm or particle detection signal. Preferably this is performed by comparing the particle size distribution to a particle size distribution signature corresponding to an particle emission event type. Over time, temporal changes in particle size distribution can also be monitored and compared to corresponding time varying particle size distribution signatures corresponding to a particle emission event type. Particle size distribution signatures (static or varying) can be empirically determined for different events.

In a second aspect there is provided a particle detector, preferably being a smoke detector, the particle detector including:
  a detection chamber for receiving a sample flow for analysis;
  a radiation source configured to emit a beam of radiation, said beam propagating across at least part of the chamber and being arranged to traverse the sample flow at a region of interest;
  an imaging system configured to capture images of the region of interest;
  a controller configured to analyse the images to determine the presence of particles entrained in the sample flow interacting with the beam in the region of interest based on scattered radiation contained in the captured images.

In a preferred form, the radiation source emits a beam of radiation having a wavelength that is sufficiently short to be scattered from air in the detection chamber to a sufficient extent that an image of the beam can be captured by the imaging system without any particles being entrained in a sample flow. Preferably the beam is in the violet or ultraviolet region of the electromagnetic spectrum.

Most preferably radiation source includes an optical system to focus the beam Preferably the beam is focused so that it converges towards the region of interest.

The controller can be configured to perform background cancellation on captured images. Background cancellation preferably involves correcting received radiation levels within a region of the image including the beam (the integration region) on the basis of a representative, received background radiation level that has been determined from at least one region of the image not including the beam. Most preferably background cancellation involves subtracting a background radiation level determined from at least one region outside the integration region from the received radiation level within the region of interest. This can include subtracting the background radiation level from the received radiation level of each pixel within the integration region or performing an equivalent calculation. Background cancellation can be performed in a piecewise fashion along the integration region using corresponding piecewise defined background cancellation regions.

Analysing the images to determine the presence of a particle includes identifying a peak in received radiation intensity in the image of the integration region. In the event that the peak is above a threshold level (e.g. based on maximum received intensity, total received energy in the peak or other suitable measure) a particle can be determined to have interacted with the beam and thus detected. Peak height (e.g. based on maximum received intensity, total received energy in the peak or other suitable measure) can also be used to infer particle size, but will also be affected by other particle properties such as light absorption or polarization scattering characteristics.

In a further aspect there is provided a smoke detector in accordance with both the first and second aspects of the present invention. Most preferably the detector includes a detection chamber and radiation source emitting a single beam of radiation. The radiation receiving system and imaging system are preferably arranged to receive radiation from a common region of interest. An embodiment of this aspect of the present invention can include any one or more of the preferable or optional features of the first or second aspects of the present invention described above.

In a preferred embodiment the controller correlates the output of the imaging system and radiation receiving system.

In a further aspect there is provided a particle detector, preferably being a smoke detector, the particle detector including:
  a detection chamber for receiving a sample flow for analysis;
  a radiation source configured to emit a beam of radiation, said beam propagating across at least part of the chamber and being arranged to traverse the sample flow at a region of interest;
  a radiation receiving system configured to receive radiation that is scattered from the beam by interaction with particles entrained in the sample flow and generate at least one output signal representing the received radiation, said radiation receiving system including, an imaging system configured to capture images of the region of interest, and at least one other radiation receiver,
  a controller configured to analyse the at least one output signal representing the received radiation to determine the presence of particles entrained in the sample flow.

Preferably the radiation receiving system is configured to receive radiation a plurality of scattering angles and in a plurality of polarisation angles with respect to a direction of propagation and known polarisation of the beam. Preferably the radiation receiving system includes a plurality of radiation receiving sensors each configured to receive radiation at a respective scattering angle. Each sensor is preferably arranged to receive radiation at a known polarisation angle relative to the angle of polarisation to the beam.

Most preferably radiation source includes an optical system to focus the beam. Preferably the beam is focused so that it converged towards the region of interest.

In a further aspect there is provided a method of determining a source of particles detected by a particle detector, the method including:

emitting light of a known polarisation such that it impinges on a stream of particles receiving light scattered from the emitted light by the particles in said stream, said light being received at a plurality of known scattering angles and polarizations;

determining at least one single particle scattering parameter based on scattered light received from single particles over a time period in which scattered light is received from a plurality of particles;

comparing light received at a plurality of scattering angles and/or polarizations and the single particle scattering parameter to a series of representative data for a plurality known types of particle; and determining that particles of at least one of said known types is present in the stream of particles on the basis of said comparison;

determining a level of particles present in the stream of particles from a given source of particles using the type or types of particles determined to be present.

Each known type of particles preferably represents a particles grouped according to at least one of the following characteristics:
particle size range;
material forming said particle.

The step of determining that particles of at least one of said known types is present in the stream of particles on the basis of said comparison, includes determining a proportion the particles in the stream being of at least one known type. Most preferably the method includes determining a proportional composition of the particles in the stream in terms of a plurality of known types of particles.

The step of determining a level of particles present in the stream of particles from a given source of particles using the type or types of particles determined to be present includes determining a relative level compared to the total level of particles. The step can include, weighting the determined proportional composition according to a set of weightings corresponding to the given source to determine the level of particles attributable to the given source.

The method can include displaying the level of particles attributed to at least one given source. The display of the level of particles attributed to a given source can be displayed in a manner that it can be compared to either other given sources or total particle level. The method can also include processing the determined level of particle attributable to the given source and generating a notification if the level meets one or more predefined criterion.

Preferably the total apparent particle brightness for a particle is determined independently of the level of light received at said plurality of scattering angles and or polarizations. Most preferably the total apparent particle brightness is determined from the output of an image capturing means of the particle detection chamber. It is also preferably that the light received at said plurality of scattering angles and or polarizations is received at a corresponding plurality of photodiodes. The a total apparent particle brightness for a particle is preferably based on a total amount of received scattered light from the particle by the image capturing means.

In some embodiments the single particle scattering parameter is a measure of central tendency of single particle scattering measurements made over the time period. A plurality of single particle scattering parameter can be generated for particles with single particle scattering parameters falling in different ranges corresponding to particles with particles with different scattering characteristics, e.g. size ranges, absorption etc.

The method can include transmitting data representing light received at a plurality of scattering angles and/or polarizations to at least one remote data processing system for the performance of a plurality of subsequent steps of the method. This can further include transmitting data from which the single particle scattering parameter is determined to at least one remote data processing server.

In a further aspect there is provided a method for determining the presence of particulate material, produced by at least one given source of particles, within an air sample, on the basis of scattered light received by a plurality of sensors in a smoke detection chamber, the method comprising:

comparing scattered light received by the plurality of sensors at a plurality of scattering angles and/or polarizations and a single particle scattering parameter to a representative data for a plurality known types of particle; and determining that particles of at least one of said known types is present in the stream of particles on the basis of said comparison;

determining a level of particles present in the stream of particles from the given source of particles using the type or types of particles determined to be present.

In one preferred form the method determines the presence of particulate material produced by an overheating wire or wires.

In another preferred form the method determines the presence of particulate material produced by a diesel engine and vented to the atmosphere in exhaust emissions.

Preferably said methods determined the level of particles produced by the given source. The level is preferably determined relative to a total level of particles detected.

Said methods are preferably performed using an embodiment of the aforementioned aspect of the present invention.

In a further aspect there is provided a system for analysing the output of a particle detection system the system including:

a data processing system configured to receive at least scattering data representing scattered light received by the particle detection system and indicating the presence of particles under analysis by the particle detection system; said data processing system being configured to process: said received data; data of a plurality known types of particle; and data representing the composition of particulate matter caused by at least one given source of particles; to generate an output representing a level of particles detected from said source by the particle detection system.

The data processing system can receive data representing light received at a plurality of scattering angles and/or polarizations and scattered light data from which a single particle scattering parameter can be determined. Said data representing light received at a plurality of scattering angles and/or polarizations is preferably derived from different light receiving components than the data from which the single particle scattering parameter(s) can be determined.

The data processing system is preferably adapted to perform data processing steps forming part of a method in accordance with any one of the previous aspects of the present invention.

In a preferred form the data processing system is located remotely of the particle detection system. The data processing system can be connected to plurality of particle detection systems to thereby enable analysis of the output of each of the systems.

In another aspect there is provided a method of modulating an beam intensity of a radiation source in a particle detector. The method includes modulating the beam intensity to produce a first number of first pulses of a first duration. The first pulses having a relatively beam intensity. The method includes modulating the beam intensity to produce a second number of second pulses of second duration. The second pulses having a lower beam intensity than the first pulses. Preferably the beam is turned off between pulses.

The method can optionally include modulating the beam intensity to produce a third number of third pulses of third duration. The third pulses having a lower beam intensity than the second pulses. Additional types of pulses and different levels can also be added.

In a preferred form, in a unit time, the first number of first pulses is smaller than the second number of second pulses. If third pulses are used, the third pulses can be less frequent than the second pulses. The first and second pulses (and also third pulses) may be interspersed with each other or grouped arranged into blocks of multiple pulses of the same type.

This modulation scheme can be used in embodiments of any one of the first to third aspects of the present invention.

In another aspect there is provided a mechanism for mounting a radiation source to a support structure. The mechanism including at least one member arranged to hold the radiation source in a position relative to the support structure, said member being selectively deformable to control the orientation of the radiation source with respect to the support structure. Said member is preferably deformable by application of heat to control the orientation of the radiation source with respect to the support structure. Preferably the mechanism further includes a heater associated with the member to selectively heat the member.

In one form the radiation source is mounted to a carrier coupled directly or indirectly to the support structure by one or more of said thermally deformable members. The carrier can be in thermal contact with the radiation source and act as a heat sink to dissipate heat created by the radiation source.

In another aspect there is provided a beam steering system for a particle detector including a mechanism for mounting a radiation source to a support structure according to an embodiment of the fifth aspect of the present invention. The beam steering system can further include a radiation sensor on which a beam emitted by the radiation emitter impinges, and a controller arranged to analyse the level of radiation received by the radiation sensor and in response to the level of radiation received, control the heating of the one or more members to thereby steer the beam. Preferably the beam is steered to maintain a substantially constant radiation level received at the radiation sensor.

In another aspect there is provided a particle detector, preferably being a smoke detector, the particle detector including:
a detection chamber for receiving a sample flow for analysis;
a radiation source configured to emit a beam of radiation, said beam propagating across at least part of the chamber and being arranged to traverse the sample flow at a region of interest;
a radiation receiving system configured to receive radiation that is scattered from the beam by interaction with particles entrained in the sample flow and generate at least one output signal representing the received radiation, said radiation receiving system including, an imaging system configured to capture images of the region of interest, and at least one other radiation receiver,
a controller configured to analyse the at least one output signal representing the received radiation to determine the presence of particles entrained in the sample flow.

Preferably the radiation receiving system is configured to receive radiation a plurality of scattering angles and in a plurality of polarisation angles with respect to a direction of propagation and known polarisation of the beam. Preferably the radiation receiving system includes a plurality of radiation receiving sensors each configured to receive radiation at a respective scattering angle. Each sensor is preferably arranged to receive radiation at a known polarisation angle relative to the angle of polarisation to the beam.

Most preferably radiation source includes an optical system to focus the beam. Preferably the beam is focused so that it converged towards the region of interest.

In an aspect there is provided a particle detector having means to control the flow rate of a sample flow entering a detection chamber of the detector. The means to control the flow can include a flow restriction or variable flow rate air movement device, such as a variable speed fan. The means to control flow can preferably substantially stop the sample flow in the detection chamber to increase the transit time of particles entrained in the sample flow across the region of interest. In some embodiments the means to control flow can be a reversible fan arranged to be reversed in order to alter flow in the detection chamber to increase the transit time of particles entrained in the sample flow across the region of interest. The particle detector is most preferably a particle detector of any type described herein.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

Further aspects of the present invention and further embodiments of the aspects described in the preceding paragraphs will become apparent from the following description, given by way of example and with reference to the accompanying drawings. In the drawings:

FIG. 2A shows a cross section taken through the chamber in the E polarisation plane of the radiation source, whereas FIG. 2B shows a cross section through the chamber taken in the M polarisation plane.

DETAILED DESCRIPTION OF THE EMBODIMENTS

Figure 1:
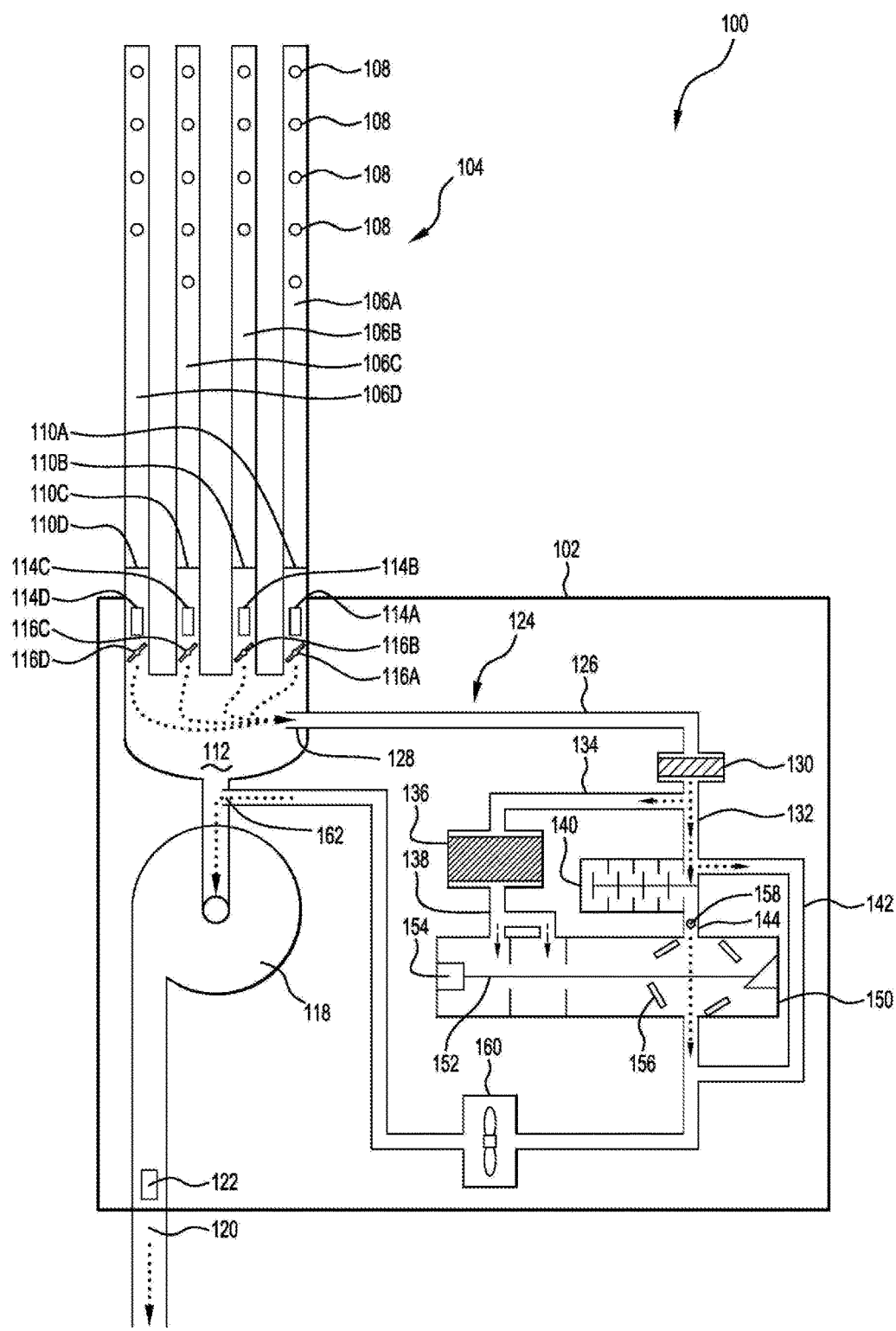
FIG. 1 illustrates, schematically, a smoke detection system according to an embodiment of the present invention.

FIG. 1 illustrates an particle detection system, in the form of an aspirating smoke detection system 100, in accordance with an embodiment of the present invention. The smoke detection system 100 includes a particle detector, in the form of a smoke detector 102 and an air sampling network 104. The air sampling network 104 comprises four sampling pipes 106A, 106B, 106C and 106D. Each sampling pipe 106A,B,C,D includes a plurality of sample inlets or sampling points 108. The sampling pipes 106A,B,C,D are coupled to respective inlets 110A,B,C,D of the smoke detector 102. The inlets lead to a plenum 112 where samples drawn from each of the sampling pipes 106A,B,C,D mix together. Each of the inlets 110A,B,C,D may include a respective flow sensor 114A,B,C,D for determining the rate of flow of sample air in the respective pipe. As will be appreciated by those skilled in the art, monitoring sample flow rate can be used to determine the operational status of the detector and sampling network 104 or be used for setting operational parameters of other components in the system. In order to assist in determining through which sampling pipe particles have been received, each inlet 110A,B,C,D can additionally be fitted with a valve 116A,B,C,D, such as a butterfly valve, which can be opened or closed to control whether samples are drawn from each individual sampling pipe 106A,B,C,D. The detector 102 includes an air movement device or aspirator 118, which is used to draw air through the smoke detection system 1000. The aspirator 118 directs air out an exhaust 120 into the environment. The exhaust can include a further flow sensor 122.

In use, air is drawn into the smoke detection system 100 through the sampling holes 108 and along the sampling pipes 106A,B,C,D into the plenum 112. The plenum can be fitted with mixing structures (not shown) which cause a mixing of sample air from each of the sampling pipes 106A,B,C,D. However, not all of the sample air is passed to the particle detection chamber 150 for analysis, instead only a subsample of the total air sample is analysed. The majority of the sample flow is passed out of the system via the exhaust 120. The air sample for analysis follows the subsampling path 124 through the detection chamber as will be described.

The subsampling path 124 begins with a sub sampling tube 126 having an inlet 128 in the plenum 112. A portion of the sample air, comprising the mixed air samples from the sampling pipes 106A,B,C,D (or whichever subset of these has its respective valves 116A,B,C,D open) enters the inlet 128 and travels along the subsample tube 126. The subsample passes through a first filter 130, at which large particles such as lint, debris and large dust particles are filtered from the sample flow. The filter 130 can include one or more mesh filters and/or coarse foam filters. The filter 130 may be set up as a 'smoke attenuator' of type described in International Patent Publication WO 2007/095675, and International Patent Publication WO 2011/106850 both in the name of the present applicant. The advantage of using such a filter is that even in the event of filter blockage, smoke particles, or other particles of interest, will still arrive at the detection chamber for detection and thus the system will fail in a safe manner.

After passing through filter 130, a portion of the sample flow continues in pipe 132 towards the detection chamber 50, without further filtration, but a second portion travels down path 134, and is further filtered by fine filter 136. The fine filter may be a HEPA filter or other filter type which removes substantially all particles from the sample flow and at its outlet produces substantially clean air. The clear air enters a clean air injection system 138 which is used to pressurise certain regions of the detection chamber of the particle detector 102 with clean air, to prevent soiling of optical surfaces by particulate matter. The portion of the flow passing down pipe 132 is again split. The first portion of this sample enters path 140 and a second portion of the sample air in pipe 132 goes via bypass path 142. Sample air in the bypass path 142 entirely bypasses the chamber of the smoke detector 102.

The portion of the sample flow in the path 140 passes through a flow control structure, e.g. a labyrinth or tortuous path in order to set an appropriate sample flow rate at the inlet 144 of the detection chamber 150. The detection chamber 150 is an optical particle detection chamber of the type described below. In a preferred form of the present invention the detection chamber 150 detects particles by measuring radiation scattering from a beam 152 of radiation emitted by a radiation source 154. A radiation receiving system, in this case including a plurality of sensors 156 cooperate to detect scattered radiation. In a preferred form of the present invention the radiation receiving system comprise one or both of:

An imaging system e.g. comprising an optical system and associated image capturing sensor;

An arrangement of multiple radiation receiving sensors arranged to capture scattered radiation at a plurality of different scattering angles (θ) in one or more polarisation planes; with respect to the plane of polarisation of the beam 152.

Further details of the detection chamber will be described below.

The inlet 144 is also provided with a flow sensor 158 to enable the rate of flow of sample air into the detection chamber 150 to be monitored. Air is drawn through the subsampling path 124 by a fan 160. The sample air drawn into the subsampling path 124 is exhausted from outlet 162 at a position downstream of the inlet 128 and drawn into the aspirator 118.

Figure 2A:
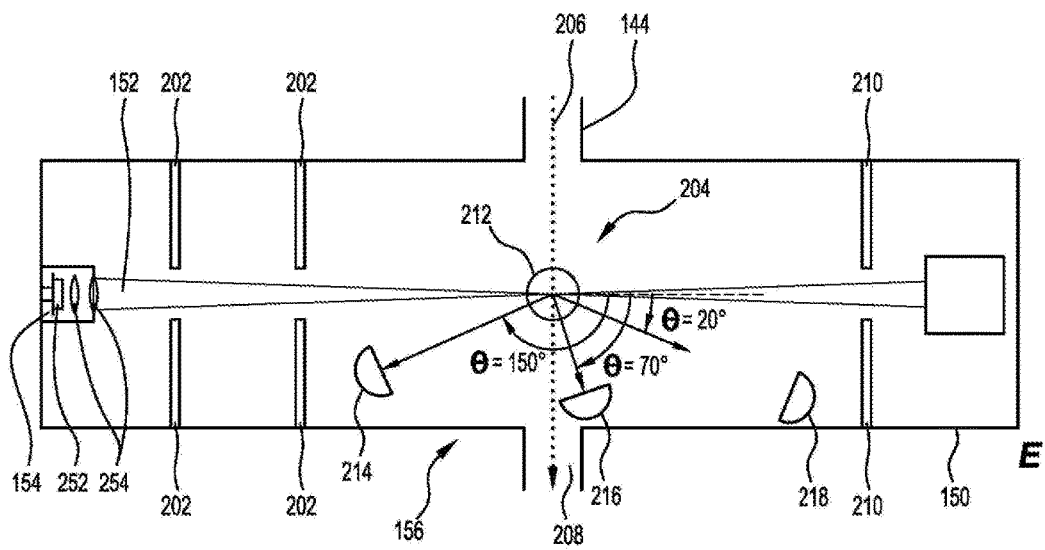
FIGS. 2A & 2B show schematic diagrams of components of the detection chamber used in embodiments of the present invention.
Figure 2B:
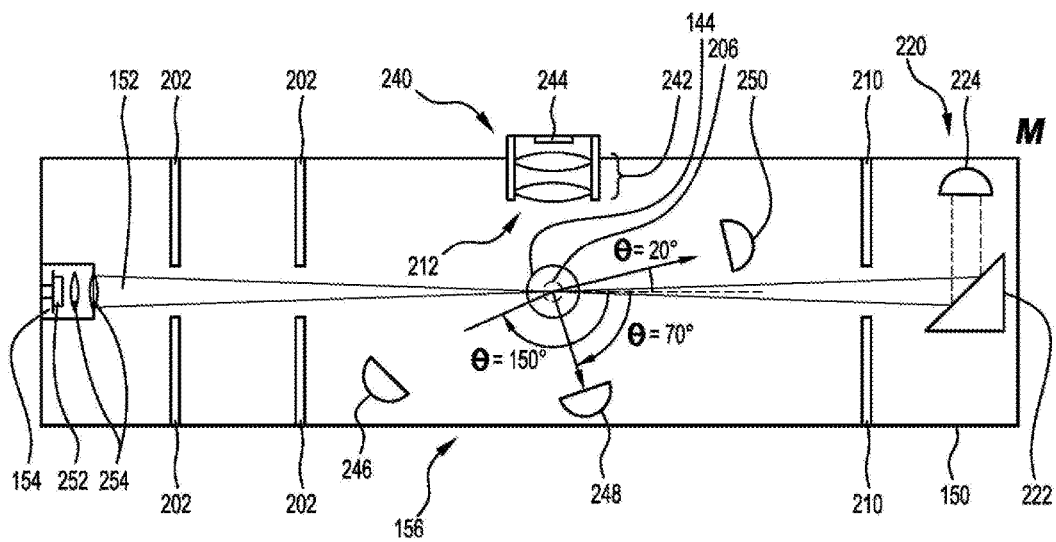

FIGS. 2A and 2B illustrate two orthogonal cross sectional views through the detection chamber 150 of the particle detector 102. As a preliminary note, the radiation source 54 is preferably a laser or other type of radiation source outputting a polarised beam of radiation 152. Throughout this document, polarisation will be described as either E plane or M plane. The E plane is defined as the plane containing the electric field vector of the beam, and the M plane is defined as the plane containing the magnetic field vector of the beam 152. In the description to follow, the illustrative embodiments are described as measuring scattered radiation in orthogonal planes coinciding with the E and M planes of polarisation of the beam. However, this need not be the case. The planes in which measurement of scattered radiation is made can be offset from each other by an angle other than 90 degrees. Moreover they need not be aligned directly with either of the E or M planes of the beam polarisation. Furthermore scattered radiation may be measured in more than two planes.

Turning to FIG. 2A which illustrates an E plane cross section through the chamber 150, the beam 152 is emitted from the radiation source 154 and passes through a series of one or more spatial filters or baffles 202, which serve to block stray, off-axis radiation and minimise background radiation within the detection chamber 150. The beam 152 is focussed such that it converges at a focal point 204 which is approximately in line with the sample flow which enters the detection chamber 150 via inlet 144, and exits the chamber via outlet 208. In the preferred embodiment the beam is about 30 µm at its narrowest point 204. The beam 152 then diverges toward the far end of the detection chamber 150. In this example the beam passes through a further spatial filter 210 and impacts a radiation absorbing structure which is used to minimise stray reflections into the centre portion of the chamber 150 and also enables beam strength and/or alignment to be accurately monitored in a manner which will be described below. The focal point or waist 204 in the beam is also aligned with a focal point of imaging optics 212 of the imaging system (not shown).

The chamber 150 includes a first plurality of radiation sensors, which in this case, comprise an array of three photodiodes to 214, 216 and 218. Each of the photodiodes 214, 216 and 218 are arranged such that their respective fields of view coincide with the intersection between the beam 152 and the sample flow 206, an area known as 'the region of interest'. Each of the photodiodes 214, 216, and 218 is set at a different scattering angle (θ) with respect to the direction of propagation of the beam 152. Photodiode 218 is set at a forward scattering angle of 20° from the direction of propagation of the beam, photodiode 216 is also set at a forward scattering angle of 70° from the direction of propagation of the beam, and photodiode 214 is set at a backwards scattering angle at 150° degrees from the direction of propagation of the beam 152. The scatter angles can be selected on an empirical basis, and maybe selected to enhance detection of certain particle types or supress detection of other particle types. For example the scattering angles used can be chosen for to enhance dust rejection, i.e. to minimise sensitivity to the presence of dust.

FIG. 2B illustrates a cross section through the detection chamber 150 in the M plane. The arrangement of the overall structure of the chamber will not be described further as it is the same as in FIG. 28. However, as can be seen better in this view, the chamber 150 includes a radiation absorbing structure 220 comprising a reflector 222, which reflects the beam towards one side of the chamber such that it is not reflected back into the central portion of the detection chamber 150. A sensor 224, which may be a photodiode or other type of radiation sensor, monitors the reflection from the reflector 222 to determine beam strength and beam alignment in a manner that will be described in greater detail below. In a preferred embodiment of the present invention, the reflector 222 is made of polished black glass or similar structure which absorbs the vast majority of radiation impinging on it, but provides a controlled reflection of radiation not absorbed. This enables photodiode 224 to view the beam without saturating. In a preferred form, approximately 1% of beam power is received at the sensor 224. Alternatively the reflector 222 may not be designed to absorb radiation and the sensor 224 provided with a filter to avoid saturation.

Towards the centre of the detection chamber 150 is located the imaging system 240. The imaging system includes an optical system 242 which in this case comprises a plurality of lenses and an image capture sensor 244. The image capture sensor 244 can be of any type, but the preferred embodiment is either a CMOS or CCD image capture chip. The optical system 242 is arranged to focus an image of the, region of interest, at the, intersection between the beam 152 and sample flow 206 onto the imaging plane of the sensor 244 such that images of the beam and radiation scattered from intersecting particles are captured by the are captured by the image sensor 244, in a manner which we described below. The M plane additionally includes a second plurality of radiation sensors 246, 248 and 250. As with the E plane, the M plane sensors 246, 248 and 250 are set at different scattering angles with respect to the direction of propagation of the beam 152. The sensor 250 set at a forward scattering angle of 20°, the sensor 248 is set at a forward scattering angle of 70°, and the sensor 246 is set at a backward scattering angle of 150°. Each of the sensors 246, 28 and 250 are arranged such that their field of view includes the region of interest.

In a preferred embodiment only a single forward scattering photo diode can be used in place of the pair of forward scattering photo diodes 250 in the M plane and 218 in the E plane. This is because at relatively small forward scattering angles, say to around 30 degrees the scattering is not strongly polarization dependent. In the case that a single forward scattering photodiode is used this can be set at any convenient polarisation angle, even part way between the E and M planes.

The radiation source 154 includes a radiation emitter 252, such as laser diode, and focussing optics 254, which are arranged with respect to each other to produce a convergent beam 152 with its focus in the appropriate position within the detection chamber 150. In the present embodiment, the emitter emits relatively short wavelength radiation in either the violet or ultraviolet range, e.g. at a wavelength of about 445 nanometers or shorter. The beam 152 is focussed towards a point 204 such that it has a "waist" at the region of interest. Most preferably the waist has a width of about 30 micrometers.

The arrangement described advantageously enables the detection of small particles with greater reliability. Moreover, it offers multiple mechanisms for particle detection and the ability to cross correlate multiple detection modalities (e.g. detection from the imaging system and one or more of the radiation receivers) in order to improve reliability of detection. On the simplest level, when one considers the individual sensors 214 through 218 and 246 to 250 alone, this provides six opportunities to detect the same particle passing through the region of interest. Use of the imaging system 240 either with or instead of the individual sensors provides another detection mechanism available to the detection chamber 150. Moreover, as will be described further below, these individual detection mechanisms can be combined in order to either improve detection reliability, detect additional information about the nature of the particles in the sample flow or detect particles at lower concentration. The additional information (as compared to single sensor systems) can aid in determining what event has caused the particles to be emitted and can thus enable a reduction in false alarms from a smoke detection system.

Figure 3:
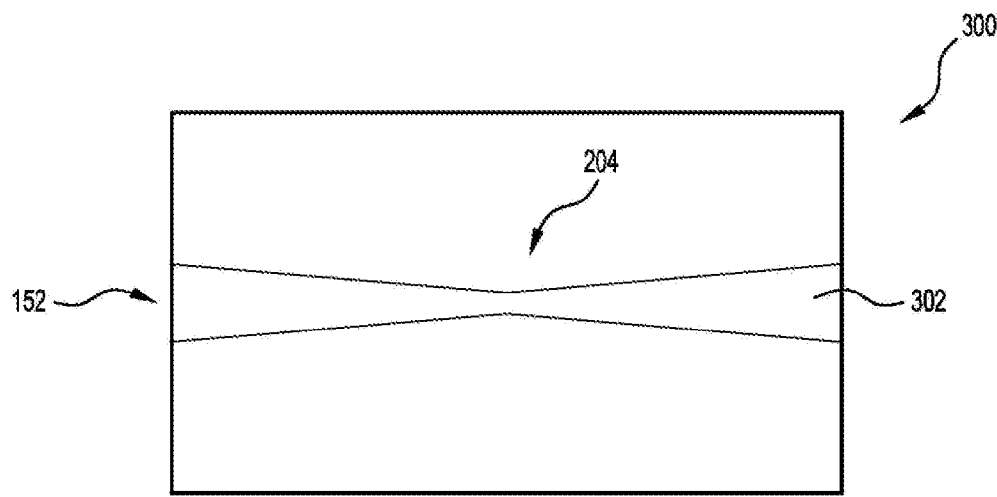
FIG. 3 is a schematic view of an image captured by an imaging system of a particle detector, according to an embodiment of the present invention, with no smoke particles present.

Turning now to the imaging system 240, FIG. 3 illustrates an image 300 as might be captured with the image sensor 244. The image 300 is captured in a situation where no particles, i.e. no dust, smoke or other particles of interest are present in the detection chamber. Even in this situation where the detection chamber contains only air, scattering from the beam is captured in the image 300. Because of its short wavelength, the beam 302 scatters from oxygen or nitrogen molecules in the air in the chamber 150 and a band, shaped like the beam, and preferably including the waist portion near the focus 204, can be seen. Advantageously, the ability to image the beam 152 directly, without the presence of any particles gives a system according to this embodiment of the present invention the ability to perform calibration in the field, at any time at which no particles are present in the sample flow or the sample flow is stopped.

Figure 4:
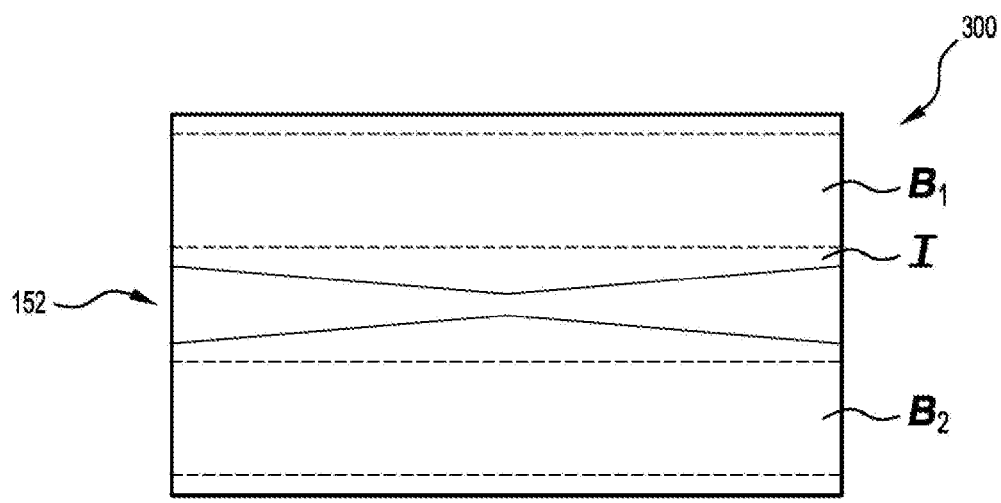
FIG. 4 illustrates an integration region and background cancellation regions used in some embodiments of the present invention to maintain calibration of smoke detector.

FIG. 4 illustrates a mechanism for performing background radiation cancellation with the detection chamber 150. Background cancellation is advantageously performed in order to compensate for an increasing level of background radiation within the detection chamber. The increasing level of background radiation arises as the walls and other optical surfaces of the interior of the detection chamber become soiled with particles from the sample flow, and as a result begin to reflect off-axis radiation within the detection chamber. Minimisation of the effect of any such stray background radiation is highly advantageous for improving detection sensitivity. In order to perform background cancellation for the imaging system 240, the image 300 has defined within it three regions. These regions are, a central integration region labelled I which contains the beam 152 and background regions B1 and B2 located either side of the integration region I. A scaling factor is calculated from the average radiation level (e.g. based on pixel value in the image) in the background regions and used to scale radiation levels detected in the region of interest. The scaling factor, S, is calculated according to the following equation:

$$S = \Sigma I - \tfrac{1}{2}(\Sigma B_1 + \Sigma B_2)$$

Where S is the scaling factor, I is the average intensity in the integration region, and B1 and B2 are the average intensities in the background regions respectively. The summation period can be set at any desired length. For example, 100 image frames, or longer or shorter such that the scaling factor can be recalculated to account for shifting background levels within the detection chamber.

If the background level is not expected to be uniform across the image, i.e. along the length of the beam, the background cancellation process can be performed on portions of the image containing beam segments along the beam's length, thereby performing piece wise background cancellation across the image 300. In extreme cases the cancellation can be performed for a single column of pixels.

The ability to perform both background cancellation and obtain a reference scattering level from air within the chamber provides particle detection using the imaging system 240 with the unique ability to have a fixed zero point and also detect system gain, thus allowing accurate particle detection, which is referrable to the fixed base line. In the field, these advantages enable a system of the present type to perform the 'smokeless' calibration, that is calibration of the detector in the field can be performed without the need for a technician to replicate smoke in order to perform calibration.

It is also worth noting that the use of the imaging sensor 244 has an inherent advantage over detection using conventional radiation sensors such as photo diodes in that each pixel of the imaging sensor 244 has low noise but the entire pixel array comprising the image sensor 244 has a very large number of pixels, meaning the overall detection system using the imaging system 240 is both low noise and captures large amounts of scattered radiation from the beam. The wide field of view of the imaging system 240 also enables spatial distinction between individual particles which may pass through the beam at any one instant. It should however be noted that in order to obtain a high sensitivity it is preferable that the sample flow through the detection chamber 150 is low. For example, the flow rate is preferably less than 1 m/s for a particle passing through the detection chamber and the volume of air passing through the chamber low. At low particle concentrations (e.g. such that would cause an extinction of the beam intensity at a level about 0.0025% per meter) it is expected that at any time only a single particle entrained in the sample flow is crossing the beam, meaning that the scattered radiation from individual particles may be resolved. Of course the instantaneous number of particles in the beam at any time is statistical in nature so overlapping detection events will occur. Moreover, at higher particle concentrations the ability to resolve scattering from individual particles will be lost. However at these higher concentration levels the certainty of detection is greater and the other detection modalities can be used more effectively.

In some embodiments it may be advantageous to enable the sample flow rate entering the chamber 150 to be actively controlled. This can be done by controlling the rate at which air is drawn through the system (e.g. by controlling the speed of the fan 118). Alternatively or in combination, the flow rate entering the chamber 150 via inlet 144 is controlled e.g. by controlling the speed of fan 160 or changing the flow path impedance, say by opening or closing a valve or the like. In particularly preferred embodiments the flow thorough the chamber can be greatly reduced, e.g. by stopping or even reversing the fan 160. This acts to increase residency time of particles in the region of interest of the detection chamber 150. This can be particularly advantageous in seeking to detect very small particles that produce little scattered light.

Figure 5:
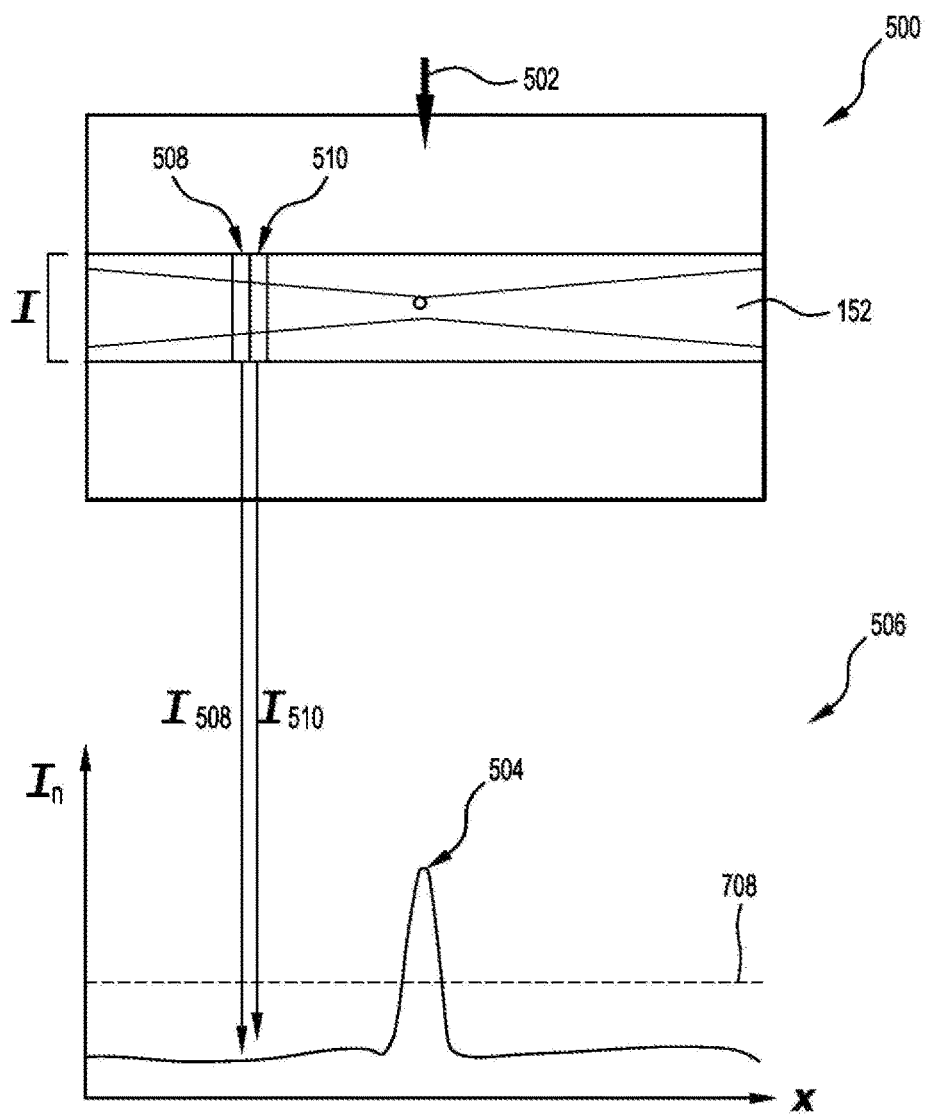
FIG. 5 illustrates the operation of the imaging system when a particle passes through the centre of the beam; and illustrates a plot of received scattered radiation intensity along the beam in the captured image.

FIG. 5 illustrates an image 500 representing a view from the imaging system 244 of the detection chamber 150, along with a plot of received radiation intensity versus position along the beam. In FIG. 5, particles move from top to bottom through the field of view of the imaging system 244 along path 502. As a particle passes through the beam 152 on path 502, radiation is scattered from the beam and captured at the image sensor 244 of the image sensing system 240. This particle detection event will cause a peak 504 in the spatial intensity distribution at a location corresponding to the position along the beam at which the particle interacts with the beam 152. In this example, the spatial intensity of measured radiation along the beam is measured by summing pixel values with a capture image for a plurality of spatial regions spaced along the length of the beam. For example, all pixel values in region 508 are summed to produce an intensity value $I_{508}$ in the plot 506. Similarly the pixels within region 510 are summed to produce the $I_{510}$ intensity value. This is repeated across each image along the length of the beam to build the plot 506. Thus effectively, the plot 506 is a histogram of summed intensities for regions of pixels grouped by position along the beam. The regions may be single columns of pixels traversing the region of interest or regions which extend both vertically and horizontally across and along the region of interest (I). As can be seen from plot 506, in a spatial position where the particle crosses the beam 152 a peak appears in plot 506.

Figure 6:
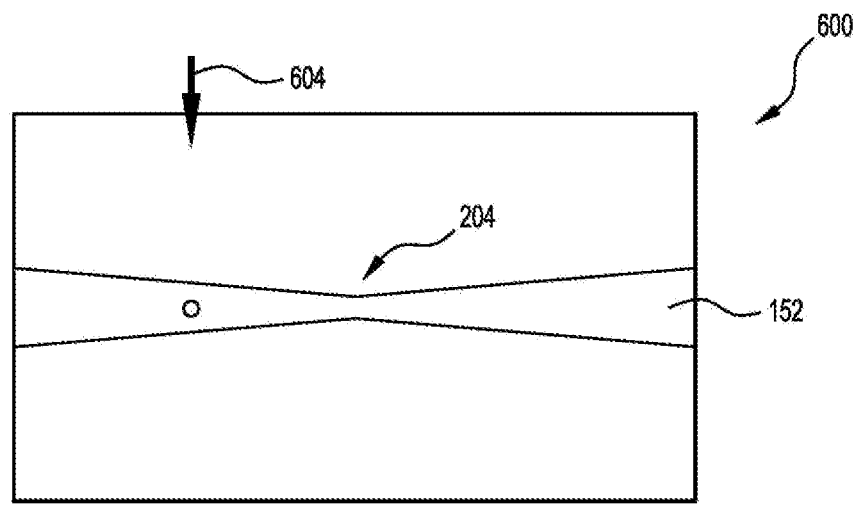
FIG. 6 illustrates similar diagrams and plots to FIG. 5, but for the case where a particle passes off centre through the beam.
Figure 6:
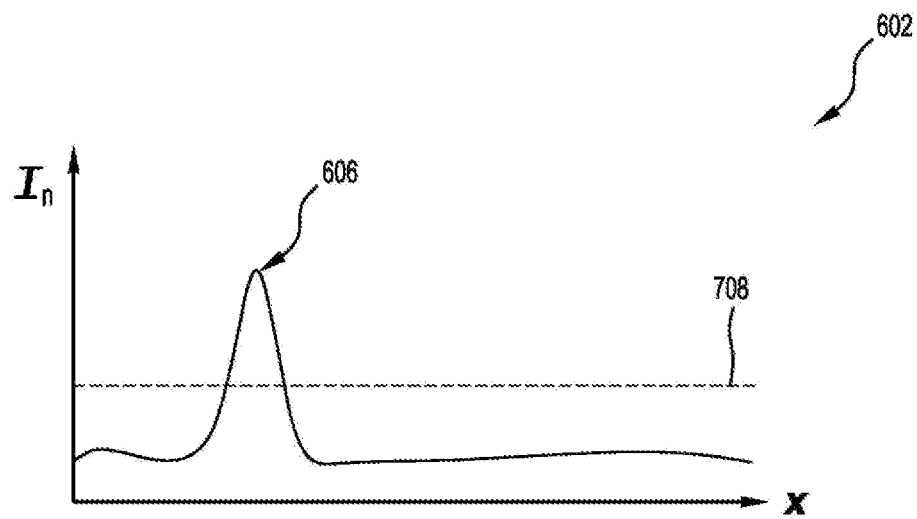

FIG. 6 illustrates a view 600 equivalent to that of the view 500 in FIG. 5 and a corresponding spatial plot 604 of received scattered radiation intensity. In this figure, the particles follow path which is not a line with the focus 204 of the beam 152 but further along the beam at position 604. Thus, the peak 606 in the intensity plot is correspondingly shifted from the centre of the position axis as indicated. This highlights an advantage of using the imaging system 240 to measure scattered radiation in the particle detector, namely, that it may be possible to distinguish between particles because they do not all follow the same path. Importantly it allows spatial resolution of multiple particles crossing the beam in a temporally overlapping fashion using the imaging system 240.

Figure 7A:
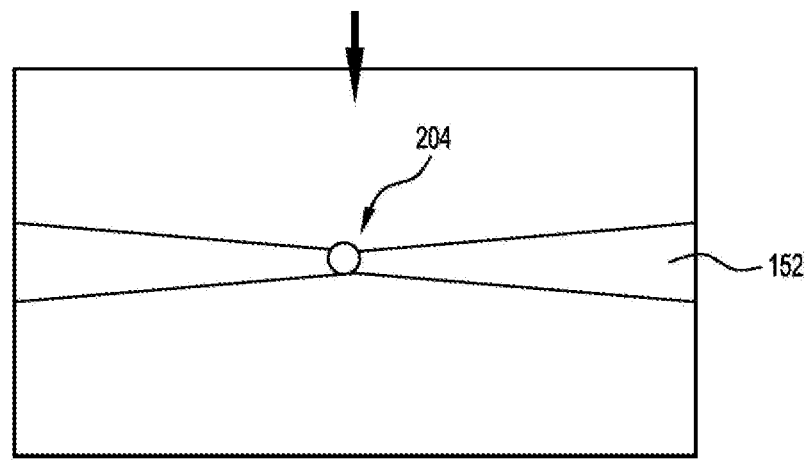
FIG. 7A illustrates a situation of a large particle passing through the centre of the beam and an associated intensity plot.
Figure 7A:
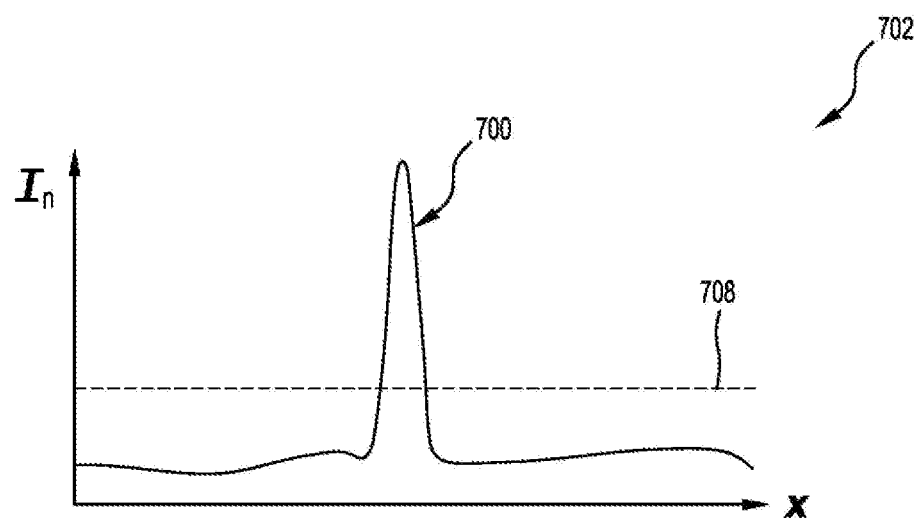
Figure 7B:
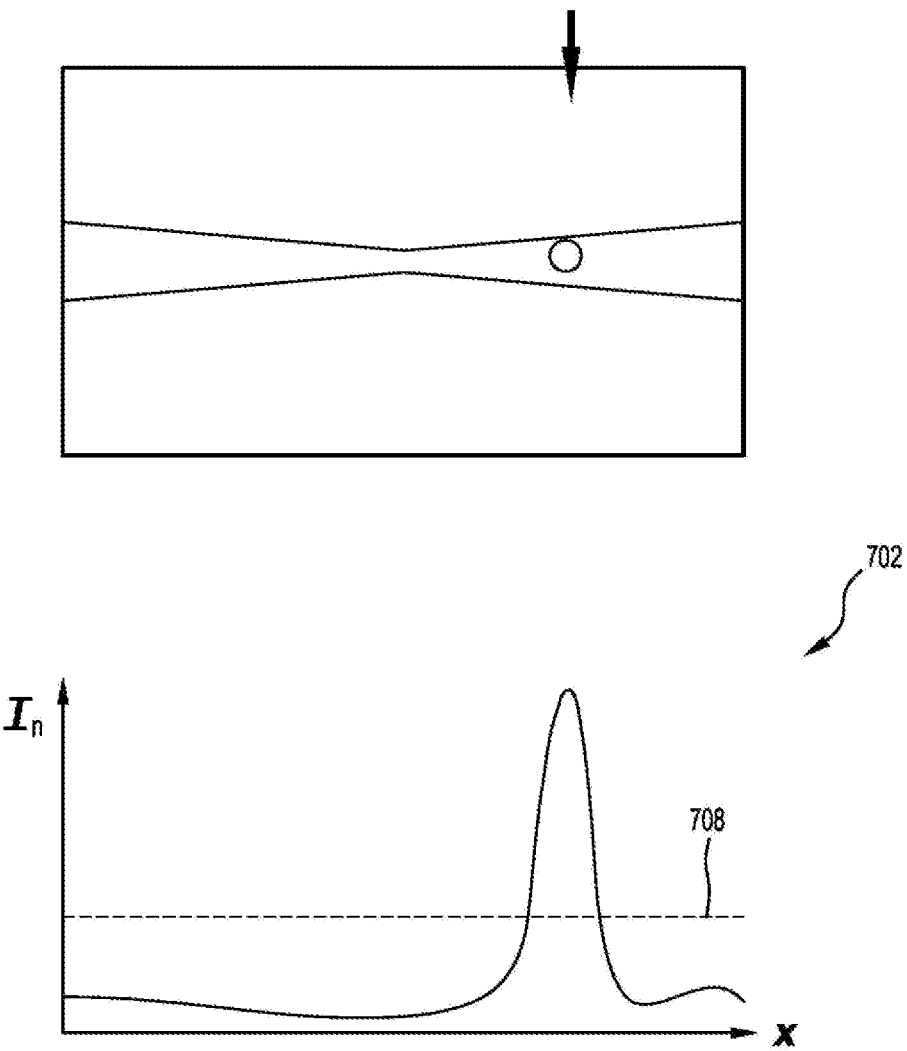
FIG. 7B illustrates a similar plot to FIG. 7A, except that the particles pass through the beam are off centre.

FIGS. 7A and 7B illustrate what happens in situations in which a large particle passes through the beam within the field of view of the imaging system 240 firstly, in FIG. 7A in line with the focus 204 of the beam 152, and secondly, in FIG. 7B, off-centre along the beam. As with FIGS. 5 and 6 the particle passing through the beam 152 produces a peak 700 in the intensity plot 702 at a spatial position corresponding to its position of crossing of the beam 152. However, when compared with the peak 504, 506 caused by a smaller particle as illustrated in FIGS. 5 and 6, the peak 700 is much larger because more radiation is scattered by the larger particle. Accordingly, particle size discrimination can be achieved by using peak height in the intensity scattering plot.

In each of the scattering intensity plots 506, 602 and 702 a threshold 708 is indicated. In embodiments of the present invention, when an intensity peak greater than the threshold 708 is identified a particle detection event is taken to have occurred. As noted above, the relatively slow flow of particles at low particle concentration and the ability to spatially resolve individual particles means that individual particle detection events can be accumulated and measured.

Figure 9:
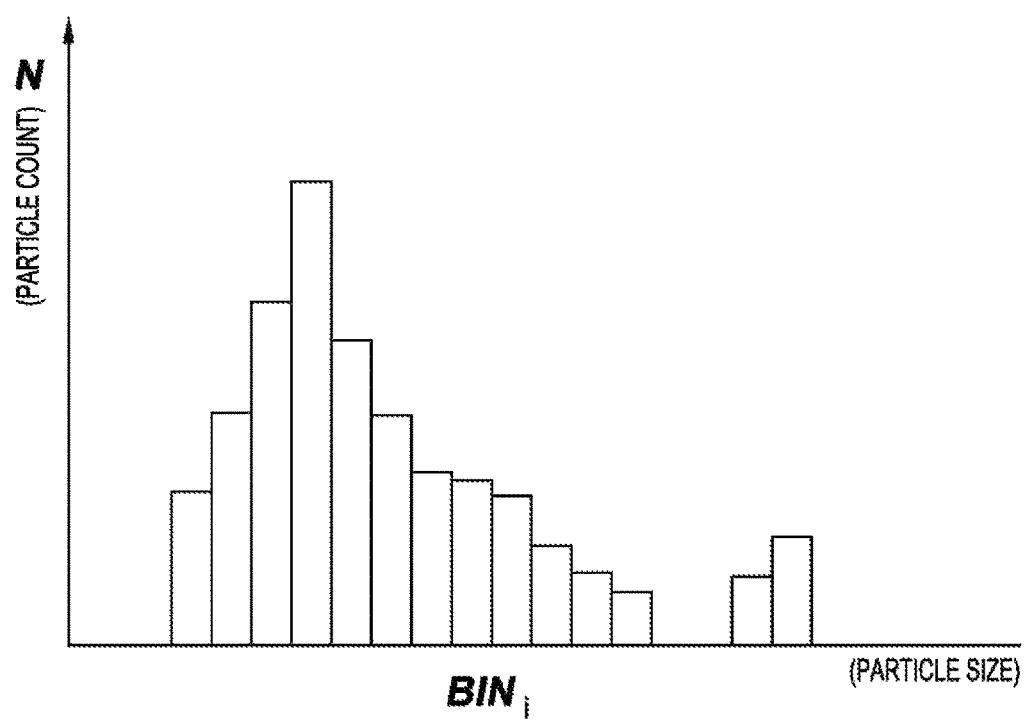
FIG. 9 illustrates a total apparent particle brightness histogram which may be used to identify the type of particle detection event occurring.

By using the peak intensity or integrating under each peak a value representing particle size may be derived from each peak, and a histogram of particle sizes or observed brightness can be created over time as illustrated in FIG. 9. As will be discussed in more detail below, this data can be used to identify the type of event which has caused the particles to be present in the sample flow. In the plot in FIG. 9 the vertical axis represents the number of times a particle in a particular size bin has been counted. The size bins are set out along the horizontal axis.

The Particle Brightness Histogram of FIG. 9 provides scattering coefficients in %/m, for particles within the parameters of each bin. In this example 80 bins are used. The binning process uses the total apparent particle brightness in an image derived from the imaging system, measured in raw imager grey levels. The particle detection threshold is set at a chosen grey level e.g. based on the noise level limitations in imager. If an image possesses a peak with a brightness exceeding the threshold level the total grey level value (G) of each particle detected measured by summing pixel grey values within the peak. This grey level value (G) is converted to dBG and rounded to the nearest integer to determine the number as follows:

$$BIN = Round(10 \log_{10} G)$$

The zero bin is used for residual bulk scatter that could not be attributed to an individual particle.

Figure 8:
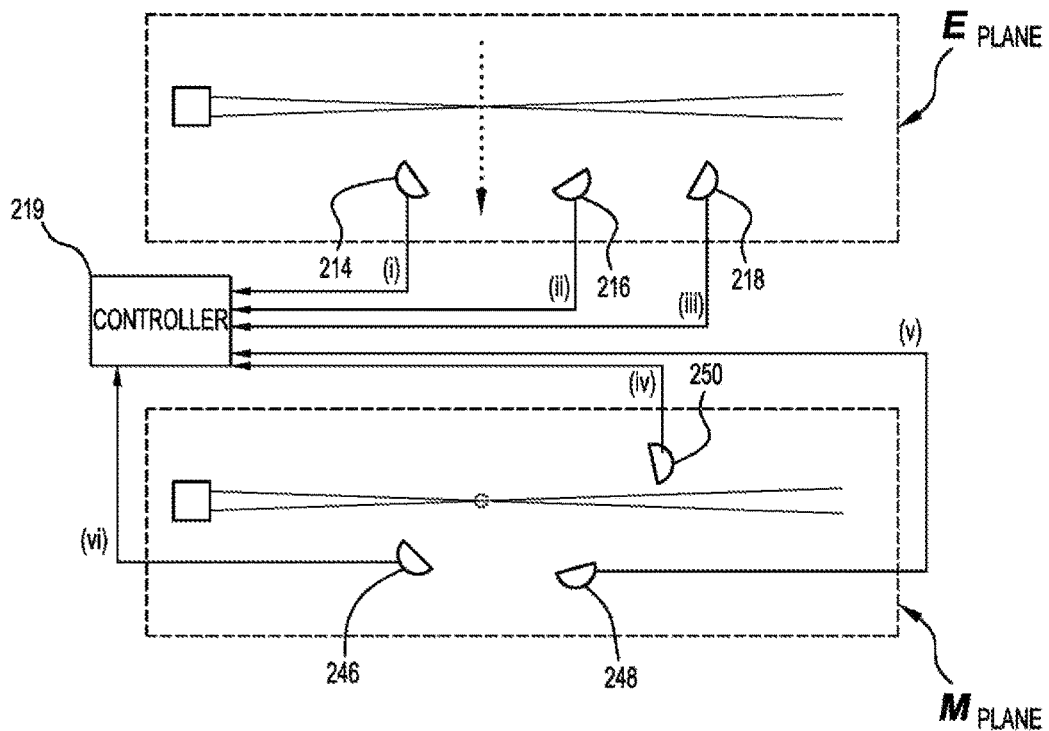
FIG. 8 illustrates schematically the arrangement of radiation sensors in each of the E and M planes of an embodiment of the present invention and plots of the sensors outputs for a plurality of particle detection events over time.
Figure 8:
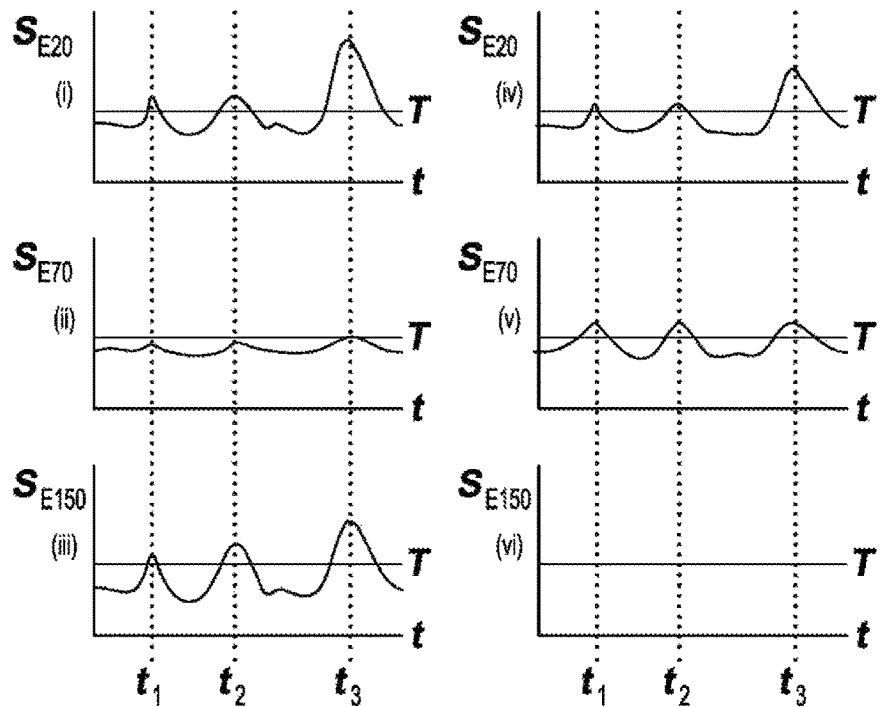

Turning now to FIG. 8 which illustrates in a more schematic fashion the E and M scattering plane detection systems of FIGS. 2A and 2B respectively. In the E plane the output of photodiodes 214, 216 and 218 are provided to the system controller 219 and are illustrated in plots I, II, III respectively. In the M plane, output of photodiodes 246, 248 and 250 the system controller 219 and are illustrated in plots IV, V and VI respectively. In each of the plots I to VI there is shown the scattering intensity S in the respective polarisation plane and at the respective scattering angle, versus time. The time period illustrated in the plots includes three potential particle detection events at times T1, T2 and T3. This can be deduced by the controller by the alignment of the peaks at three times T1, T2 and T3 in each of the plots I to VI. As can be seen the event at time T1 produces a relatively small peak in plots I, III, IV, V and VI but is almost flat in plot II. Similarly the plots of the peaks aligned at times T2 and T3 are of different sizes in the different scattering angles and at different polarisation angles.

By comparing the level of measured scattering at the same angle in the different polarisation planes for each scattering event, the system controller 219 can determine a particle size for each particle detected. Again as previously noted, due to the relatively low rate of sample flow through the region of interest of the particle detector and the small size of the region of interest, at least at low particle concentrations, it is possible to detect individual particles passing through the beam. Each plot I, to VI has marked on it a threshold T above which particle detection event is deemed to have occurred. It will be noticed that in plot II the peaks at time T1 and T2 do not exceed the threshold value. However because the threshold value T is crossed at other scattering angles or polarisation angles the particle detection event may still be detected and identified by the controller 219. In an alternative to using a straight intensity threshold T to determine whether a particle has been detected instead, other detection methodologies may be used for example by integrating the total scattered energy within a pulse and comparing this to a predetermined value. In the preferred embodiment, the particle detector is an aspirating smoke detector used to determine the presence of a fire. Ideally, the smoke detection system is able to detect fires at a very early stage. Using a histogram of the type illustrated in FIG. 9 it is possible to identify with more certainty that a fire is in fact alight or about to become alight based on the particle size distribution represented by the histogram. Certain fire types produce particles having a characteristic particle size distribution, which can be matched to the measured histogram. Moreover, in some embodiments it is possible to track the development and change in the measured histogram over time to identify a pattern of progression in particle size distribution that indicates a particular type of fire or characteristic of fire development. These mechanisms can be used to determine with more certainty whether particles that are being detected are indicative of fire or are nuisance particles and might be ignored.

Once particle concentration increases to a higher level, the ability to resolve individual events at an intensity level above the threshold T is lost, since many detection events overlap in time. At this time the output of one, all or a subset of the sensors will essentially always be above the threshold level. This enables the signal processing to become similar to that of a more conventional radiation scattering particle detector. In conventional radiation scattering smoke detectors a threshold radiation scattering level is set and when the short term average level of measured scattered radiation exceeds the threshold for a predetermined time period, smoke is taken to be detected. Several thresholds may be set for different alarm levels. Thus, in some embodiments of the system described herein, once the concentration of particles in the air sample becomes so high that the controller can no longer reliably temporally distinguish particle detection events in the sensor(s) output (or a combination of sensors' outputs) a short term sensor reading (or a combination of sensors' outputs) can be compared to a threshold or set of thresholds to determine alarm events, or alarm levels.

As will be appreciated by the above description, in a preferred forms a particle detector according to the above aspects and embodiments enables multiple measurements of particle properties to be determined. In particular the preferred embodiments provide at least one single particle scattering parameter (e.g. based on total scattered energy) as measured by an imager, and additional measurements of scattering intensity at various angles and polarisations, measured by the photodiodes. Such a suite of measurements can be used to provide new functionality over conventional detectors, for example information about the type of particles present in sample, and to issue notifications based on that information. Moreover this can be used to infer the source of the particles. For instance, black smokes from liquid fuel fires might be discerned from the pale smoke from a cellulose fire. Different alarm or notification thresholds and delays might be appropriate for each differentiable smoke type, depending on the application environment and the likely nuisance materials.

Accordingly, in a further aspect the present invention provides a method of determining a source of particles detected by a particle detector, the method including: emitting light of a known polarisation such that it impinges on a stream of particles; receiving light scattered from the emitted light by the particles in said stream, said light being received at a plurality of known scattering angles and polarizations; determining at least one single particle scattering parameter over a time period in which scattered light is received from a plurality of particles; comparing light received at a plurality of scattering angles and/or polarizations and the single particle scattering parameter to a series of representative data for a plurality known types of particle; and determining that particles of at least one of said known types is present in the stream of particles on the basis of said comparison; determining a level of particles present in the stream of particles from a given source of particles using the type or types of particles determined to be present.

Turning now to the data analysis, preferred embodiments provide at least one of the following functions:

Categorization of the types of particles present in the sample analysed by the detector. The categorizations of type of particles can represent known particle types that have been grouped according to a wide range or parameters, for example, a particle size range, particle colour; the material forming said particle. The categorization process could include determining a proportion the particles in the stream being of one or more of the types that are of particular interest. It could also involve determining the fractional composition of the particles in according to a plurality of known types of particle.

Correlation of the particle types with a threat and/or nuisance database created for at least one each application. The threat and/or nuisance databases could for example indicate a set of weightings for each threat or nuisance particle source which is used to determine the level of particles attributable to the given source. Thus the process can include determining a level of particles present in the sample under analysis that are attributable to a given source of particles.

Reporting at least one of the correlation and the corresponding action to take determined by the threat database. This can involve displaying the level of particles attributed to at least one given source e.g. a particular threat or nuisance. The display of the level of particles attributed to a given source can be displayed in a manner that it can be readily compared to either other given sources or total particle level. The reporting can also include generating an automated notification if the level meets one or more predefined criterion. This process can be similar to issuing alarm or alert signals in other types of smoke or gas detection. Reporting the results can be performed continuously or at a trigger alarm level. In some embodiments the reporting includes sending a trigger signal to another system that acts on the signal and takes a particular action, such as triggering an alarm, sending a message, activating a related system to ameliorate the condition, such as activating a filter or exhaust fan etc.

Figure 10:
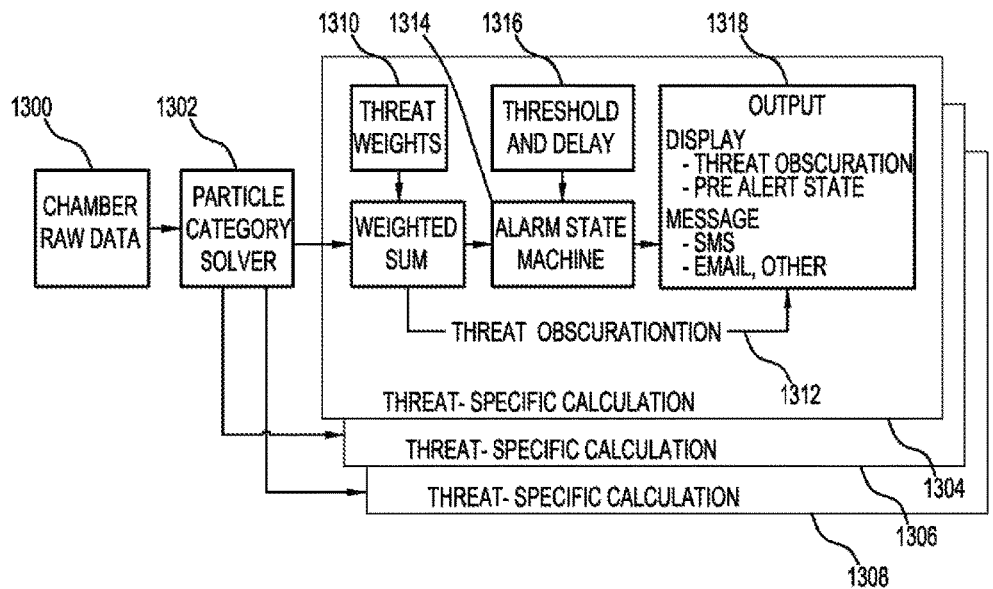
FIG. 10 schematically illustrates the dataflows in a particle type analysis process used in some embodiments.

FIG. 10 schematically represents the data flows in one embodiment of analysing the output of a particle detection system of the types described herein. In the present example the particle detection system has a particle detection chamber of the type described in FIGS. 2A and 2B but modified to have slightly different scattering angles in the E and M plane and to use only a single forward scattering photo diode in place of the pair of forward scattering photo diodes 250 in the M plane and 218 in the E plane. The single forward scattering photodiode is set at a polarisation angle of about half way between the E and M plane to receive light at a scattering angle of 30 degrees. The output of this photodiode is termed the forward random measurement. A side scattering photodiode is used in each of the E and M planes and are set at a scattering angle of approximately 90 degrees. The outputs of these photodiodes are termed the Side E and Side M measurements respectively. A backwards scattering photodiode is used in each of the E and M planes and are set at a scattering angle of approximately 150 degrees.

In the example, raw scattering output 1300 is provided by the detection chamber to a particle category solving module 1302. The output of the particle category solving module 1302 indicates whether particles of at least one of known type is present in sample. In this example this takes the form of outputting one or more sample fractions identifying the fractional contribution to the total particle load of at least one type or class of particle. This output can then be analysed by one or more threat or nuisance calculation modules 1304, 1306, 1308 (preferably in parallel). The threat or nuisance calculation modules determine a level of particles present in the sample under analysis from a given source of particles. Each threat or nuisance calculation module 1304 to 1308 applies a set of specific threat or nuisance weightings 1310 to the particle fractional contributions to generate an obscuration level 1312 that is caused by the treat or nuisance of interest. This output can be provided to an alarm state machine 1314 which is configured to apply treat-specific or nuisance-specific alert logic, for example based on a set of predefined threshold or delay values 1316.

System outputs 1318 can then be made on the basis of the output of the alarm state machine 1314 and/or threat obscuration data 1312.

For example the outputs could include a graphical user interface indicating, any one or more of:

A threat-specific or nuisance-specific obscuration level,
An alert state based on the threat-specific or nuisance-specific obscuration level.

Such data could be provided alongside or alternately with corresponding total obscuration data and underlying system alarm state data. For example a visual display of total obscuration and a fractional obscuration caused by a specific threat (e.g. particles generated by overheating wires) can be made together to enable a user of the system to more easily perceive a likelihood that the a threat of particular interest to a user (overheating wire(s) in this example) is the cause of particle emissions. Similarly a visual display of total obscuration and a fractional obscuration caused by a specific nuisance (e.g. particles generated by a diesel powered engine) can be made together to enable a user of the system to more easily perceive a likelihood that particles being detected are caused by the nuisance source and not a threat.

In addition or alternatively, the threat or nuisance calculation modules 1304, 1306, 1308 can issue alert messages when predefined criteria are met. Such messages can be, for example, email or SMS messages to designated users or user groups.

The following description provides additional detail of the function of the modules discussed above. The raw data from the detection chamber 1300 is provided to the particle category solver 1302 periodically, say about once per second. The primary data received includes:

A smoke obscuration value;
Smoke type factor computed by the detection chamber control system based on the ratios of scattered light received at different scattering angles and/or polarizations;
A plurality scattering ratios, being ratios of scattered light received at pairs of photodiodes of the analysis chamber at different scattering angles and/or polarizations. In most embodiments the scattering ratios relate to bulk scattering from the beam, rather than for temporally resolved interactions between particles and the emitted light. In the present illustrative embodiments the ratios used are:
Side E to Side M (SESM)
Back E to Back M (BEBM)
Forward Random to Side E (FRSE)
Side E to Back E (SEBE)
Particle Brightness Histogram, (80 element array)
Detector Faults The four ratios in the illustrative example are derived from the 5 photodiodes oriented in the E plane, M plane and Random (mixed) polarisation positions (i.e. neither E or M plane) and either in forward scatter (~30 deg) side scatter (~90 deg) and back scatter (~150 deg).

The Particle Brightness Histogram provides scattering coefficients in %/m, for particles within the parameters of each bin. In this example 80 bins are used. And the histogram is generated on the basis of the output of the imaging system of the detection chamber in the manner described above. The total amount of received light scattered from a particle and received by the imaging system will be strongly dependent on the particle's size, but will also be affected by other scattering properties of the particles such as their absorption and polarisation scattering characteristics. Thus in some instances the particle brightness histogram could also be used as a histogram of particle size estimations for a plurality of particles.

The binning process in the present example uses the total apparent particle brightness in an image derived from the imaging system, measured in raw imager grey levels. The particle detection threshold is set at a chosen grey level e.g. based on the noise level limitations in imager. If an image possesses a peak with a brightness exceeding the threshold level the total grey level value (G) of each particle detected is measured by summing pixel grey values within the peak. This grey level value (G) is converted to dBG and rounded to the nearest integer to determine the bin number, so, $$BIN=\text{Round}(10 \log_{10} G)$$

The zero bin is used for residual bulk scatter that could not be attributed to an individual particle. Notionally this zero bin can be attributed to scatter off air or gas molecules (when no other particulate material is present) or if the level rises above the background level an additional scattering contribution from very small particles.

The Particle Category Solver 1302 receives this raw data and computes fractional scattering attributable to a set of particle categories (Smoke Category Fractions).

In the current example there are seven categories:
Dust (All dust types)
Overheating (electrical insulation pre-combustion)
Pyrolysis (cellulose pre-combustion)
Flame (cellulose flaming or smouldering at moderate temperature)
Soot (black smoke, large particles, typically flaming liquid fuel or plastics)
Fine Soot (black smoke, small particles such as diesel exhaust)
Nano (very small particles and large gas molecules e.g. refrigerants)

The Nano category is derived directly from bin zero of the particle brightness histogram. The other six categories are obtained by computing a solution of a set of simultaneous equations.

After the initial equation solving, the results are then re-normalised to include the Nano component. In some embodiment the results can be re-normalised again with an adjusted dust proportion that has been separately derived using another dust level estimation mechanism, but this is not preferred.

In the present embodiment the equation solver component of the particle category solver module 1302 deals with 6 input variables, 6 equations and solves for 6 unknowns. The raw inputs are the five scatter measurements (i.e. one for each of the 5 photodiodes in the example,) and one single particle scattering parameter derived from the imager output histogram.

Since the system is linear, and only the scattering ratios are received as input data, one of the scatter measurements is assigned a value of 1 arbitrarily. Although, it would be possible to recast the problem as a rank 5 equations set)

The five scatter measurements are calculated from the ratios, as follows, normalised to the value of SM.

$$SM=1.0$$

$$SE=SESM \cdot SM$$

$$BE=SE/SEBE$$

BM=BE/BEBM

FR=FRSE·SE

The single particle scattering parameter is determined from the particle brightness histogram. In this example the single particle scattering parameter is a measure of central tendency of particle brightness measurements in the histogram. A plurality of single particle scattering parameters can be generated for different regions (e.g. bands of contiguous bins) of the histogram. The different regions of the can be viewed represent particles having similar scattering properties. However, in the present example only one single particle scattering parameter is determined. The single particle scattering parameter used in the present example is computed as the centre of gravity of the single particle scattering parameter, not including the zero bin.

$$SZ = \sum_{b=1}^{79} b \cdot H_b \Big/ \sum_{b=1}^{79} H_b$$

Where b is the bin number and $H_b$ is the count in the corresponding brightness histogram bin.

Once the input parameters are established a solution of the set of simultaneous equations can be found. The six input and output parameters can be represented by column vectors Y and X $$Y = \begin{bmatrix} SM \\ SE \\ BE \\ BM \\ FR \\ SZ \end{bmatrix} \quad X = \begin{bmatrix} X_0 \\ X_1 \\ X_2 \\ X_3 \\ X_4 \\ X_5 \end{bmatrix}$$

Where the relative quantities (i.e. fractions) of each particle type (Dust; Overheating; Pyrolysis; Flame; Soot; Fine Soot) are the $X_0 \ldots X_5$ Six sets of values (similar to the vector Y) that represent "ideal" smoke types are used as basis vectors $B_0 \ldots B_5$ to form a matrix A $$A = [B_0 B_1 B_2 B_3 B_4 B_5]$$

Then the equations relating the raw observed values to the smoke categories can be written as:

$$Y = AX$$

This standard set of simultaneous equations can be solved in many ways, for example using a simple matrix inversion technique.

$$X = A^{-1} Y$$

This has the advantage of simplicity, and is very fast once $A^{-1}$ has been computed. The matrix inversion only needs to computed once since the basis vectors are constant.

In an exemplary form the values for the basis vectors can be as follows:

$B_0 = \{1, 0.865, 0.302, 0.281, 1.815, 53.0\}$ for Dust $B_1 = \{1, 0.895, 0.464, 0.239, 5.048, 45.0\}$ for Overheated Insulation $B_2 = \{1, 1.195, 1.045, 0.578, 4.314, 49.5\}$ for Pyrolysis $B_3 = \{1, 0.556, 0.192, 0.148, 0.959, 41.0\}$ for Flame $B_4 = \{1, 0.178, 0.242, 0.251, 0.313, 43.0\}$ for Soot $B_5 = \{1, 0.316, 0.418, 0.388, 0.727, 34.0\}$ for Fine Soot Note that as presented above, each line represents one column vector of A.

Is will be appreciated that intensities in dbG are dependent on the specific laser power and wavelength, optics and imager chip used. The scattering ratios in the basis vectors are also implementation dependant, however the basis vectors set out above may be used in a detection chamber having the following geometry:

| Photodiode | Scattering angle (degrees)) | Distance of photodiode to centre of region of interest |
|---|---|---|
| SM | 90 | 10 mm |
| SE | 90 | 10 mm |
| BE | 150 | 15 mm |
| BM | 150 | 15 mm |
| FR | 30 | 20 mm |

Basis vectors for other implementations can be determined empirically as would be understood by the person skilled in the art.

The output from this stage is a vector X representing the fraction of each particle type present in the analysed sample, with the total of the factions adding to 1. However, this six variable solution does not include the "Nano" particle category. This is then added as a seventh element to the solution by scaling and re-normalisation.

Generally speaking this is done by calculating the "nano" category's contribution to the total scattering then scaling down the values of the vector X proportionately. This enables the solution to be expanded to a seven variable solution including the scaled values from X and the "nano" category's contribution. In the preferred embodiment this is performed as follows:

$N = H_0$ for $H_0 > 0$, else 0    (nano particle obscuration)

$SO = FS \cdot \sum_{bin=1}^{79} WT_{bin} \cdot H_{bin} + N$  (total obscuration)

$XS = \sum_{n=0}^{5} X_n$    (the sum of X excluding the nano catreogy)

$FN = N/SO$    (fraction of total obscruation due to nano)

$k_1 = (1 - FN)/XS$    (normalisation factor)

$F_{0..5} = k_1 \cdot X_{0..5}$    (normalised category fractions)

$F_6 = FN$    (fraction due to nano)

Note that $\sum_{n=0}^{6} F_n = 1$

Where $H_i$ is the histogram count in the ith bin and WT is a total obscuration weight for each bin and obtained by piecewise linear interpolation from the following table:

| dB(G) | WT |
|---|---|
| 0 | 1 |
| 16 | 1 |
| 20 | 6 |
| 30 | 2 |
| 40 | 2 |
| 55 | 2 |
| 56 | 2 |
| 79 | 2 |

The output of this phase of the process is a 7 element vector F containing fractions of each of the 7 contributions including "nano" particles, 5 smoke types and dust. Thus, F effectively reflects the proportional composition of the particles in the sample in terms of a plurality of the known types of particles. With any one element in the vector reflecting the proportion of the sample contributed by a given one of the particle types.

In the next step threat or nuisance calculations (1304, 1306 and 1308) can be performed to determine a level of particles present in the sample arising from a given source of particles can be performed.

Using a threat as an example. In order to produce a threat level for a given scenario, the previously calculated smoke type fractions are multiplied by threat weighting factors ($TW_n$) corresponding to a predetermined threat of interest (it should be noted that the term threat weighting factor is chosen for descriptive purposes only and the weighting factors $TW_n$ can equally be used to enhance detection or reporting on particle sources that are not a direct threat, but might be usefully identified e.g. because they are a nuisance or for some other reason). For example, if a pre-alarm or notification indicative of the presence of diesel exhaust is desired the threat weighting factors (1310) will place most of the weight on the Fine Soot category, and a smaller weight on Soot, since depending on the particular vehicles, both categories may be present.

In many cases where one particle type only is of interest the threat weighting factors will be 1.0 for the one category of interest and 0 for the rest. In some embodiments it is possible to use negative weights. For example, a liquid fuel fire pre-alarm might use a weight of 1.5 in Soot and −0.5 in Fine Soot. Threat weighting factors of this type will increase responsiveness to soot particles and reduce the response to diesel smoke that might also be present in the environment.

In preferred embodiments the weights should not normally exceed unity, since the threshold in the Alarm State Machine should be used for overall sensitivity.

These weights are when multiplied by the Total Obscuration yield the Threat obscuration as follows:

$$T = TO \cdot \sum_{cat=0}^{6} TW_{cat} \cdot F_{cat} \quad \text{(threat obscuration)}$$

To give some more concrete examples exemplary threat weighting factors that may be used to enhance detection or identification of particles from certain causes are set out in the table below.

TABLE 1

| Threat or nuisance source | Threat weighting factors per fraction ||||||| Alarm state machine configurations ||
|---|---|---|---|---|---|---|---|---|---|
| | Dust | Over-heating | Pyrolysis | Flame | Soot | Fine Soot | Nano | Threshold (obs %/m) | Delay (s) |
| Diesel Engine Exhaust[1] | 0 | 0 | 0 | 0 | 0.5 | 1 | 0 | 0.1 | 10 |
| Liquid Fuel[2] | 0 | 0 | 0 | 0 | 1.2 | −0.6 | 0 | 0.1 | 5 |
| General Fire Pre-Alert[3] | 0 | 1 | 1 | 1 | 0.25 | 0.25 | 1 | 0.05 | 10 |
| Dust Warning | 1 | 0 | 0 | 0 | 0 | 0 | 0 | 0.05 | 10 |
| Electrical Arcing[4] | 0 | 0 | 0 | 0 | 0 | 0 | 1 | 0.02 | 20 |
| Insulation Overheating | 0 | 1 | 1 | 0 | 0 | 0 | 0 | 0.02 | 20 |

It footnoted in the table it has been found in empirical testing that:

1) Diesel engine exhaust spans both the Soot and Fine Soot categories.
2) Liquid fuel fires tend to produce much more Soot than Fine Soot, the values shown should therefore reduce the response to diesel engine exhaust while maintaining sensitivity to the larger black particles.
3) A General Fire Alert might benefit from reduced response to the black smokes in an environment where diesel engine exhaust may be present. This is an example of using the present method to minimise the impact of a source of nuisance particles on the smoke detection process.
4) Under laboratory conditions it has been observed that electrical arcs producing very small particles.

Further empirical testing can be used to refine or tailor the above threat weighting factors for different calculations, or add new categories of interest.

The next phase of the method involves using the threat obscuration values for generating system outputs and/or reporting. This process is performed using the alarm state machine 1314. In its simplest form this may take the form of using an alarm state machine based on a simple threshold and delay, as will be known to people skilled in the art. In such systems a notification is issued if the Threat Obscuration exceeds a predetermined Threshold for more than the Delay period. Table 1 includes an exemplary alarm threshold and delay for the six example threat or nuisance sources.

Is some implementations, since the present analytic methods are not used as the primary analysis for issuing particle detection alarms, alerts can be cleared automatically when the Threat Obscuration decreases below the Threshold, although to prevent multiple alarms for the same threat where a rapid fluctuations occur a delay between repeat alerts could be implemented.

As will be appreciated by those skilled in the art, it will be necessary to generate an output to enable downstream actions to be taken based on the above particle detection analysis.

The outputs can be made directly to another system or system component to enable automatic action to be taken by the other system or system component. Alternatively or additionally the outputs can be made in a human readable form, e.g. as part of a GUI or other user interface to enable a user to make decisions based on the system output. Examples of these will now be given.

In a preferred embodiment a graphical user interface is provided which provides a graphical representation of the selected threat or nuisance source.

Figure 11:
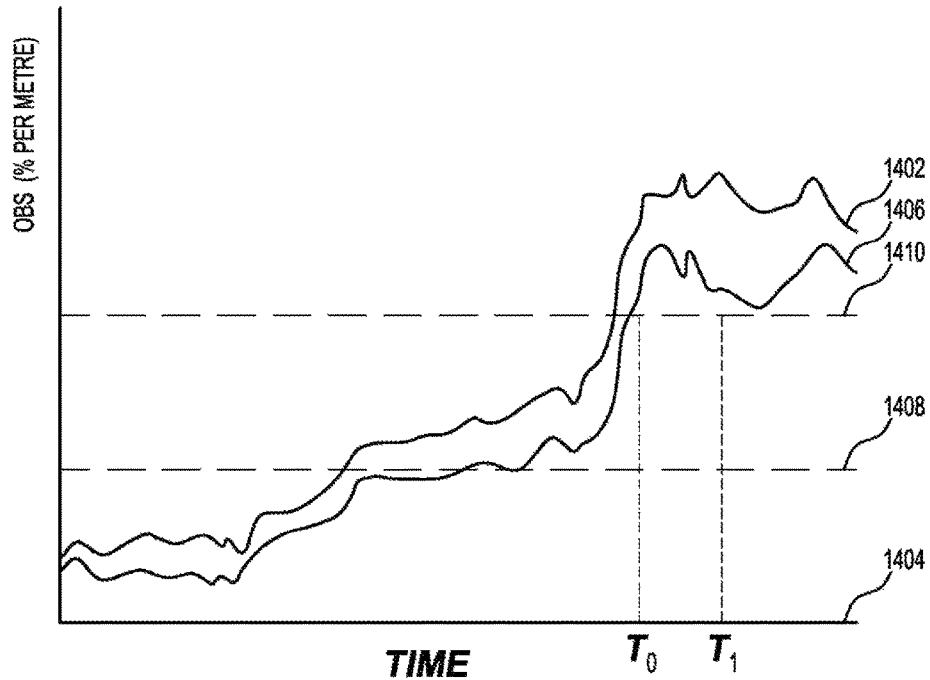
FIG. 11 illustrates a graphical user interface element useable in one some embodiments.

FIG. 11 illustrates an exemplary portion of the user interface showing graph 1400 total detected obscuration over time 1402 and the obscuration caused by dust over 1404 time and the obscuration caused by diesel smoke 1406 over time. The plot also illustrates the dust alert threshold 1408 and diesel emissions alert threshold 1410. Using an interface of this type it is relatively easy for a user to interpret that the detected increase in total obscuration is being caused by an increase in diesel smoke, but that dust levels are low.

As can be seen, at time $T_0$ the diesel particulate levels exceed the threshold 1410 and at time $T_1$, that follows after an expiry of a predetermine delay period, an alert is issued to the appropriate system user to notify them of the high level of diesel emissions. The alert can be of any known type, and may be any visible or audible indication that an alert threshold has been exceeded. In preferred forms the system sends an electronic communication to a designated user, e.g., via text message, email or other mechanism.

The user can use this information to take appropriate action, such as identify the source of diesel exhaust (e.g. a vehicle operating in the area being monitored or the starting of a diesel generator) and if appropriate or necessary take steps to stop the emission of the diesel exhaust. Other related actions might also be taken, say to activate an exhaust fan system to disperse the airborne particles.

Figure 12:
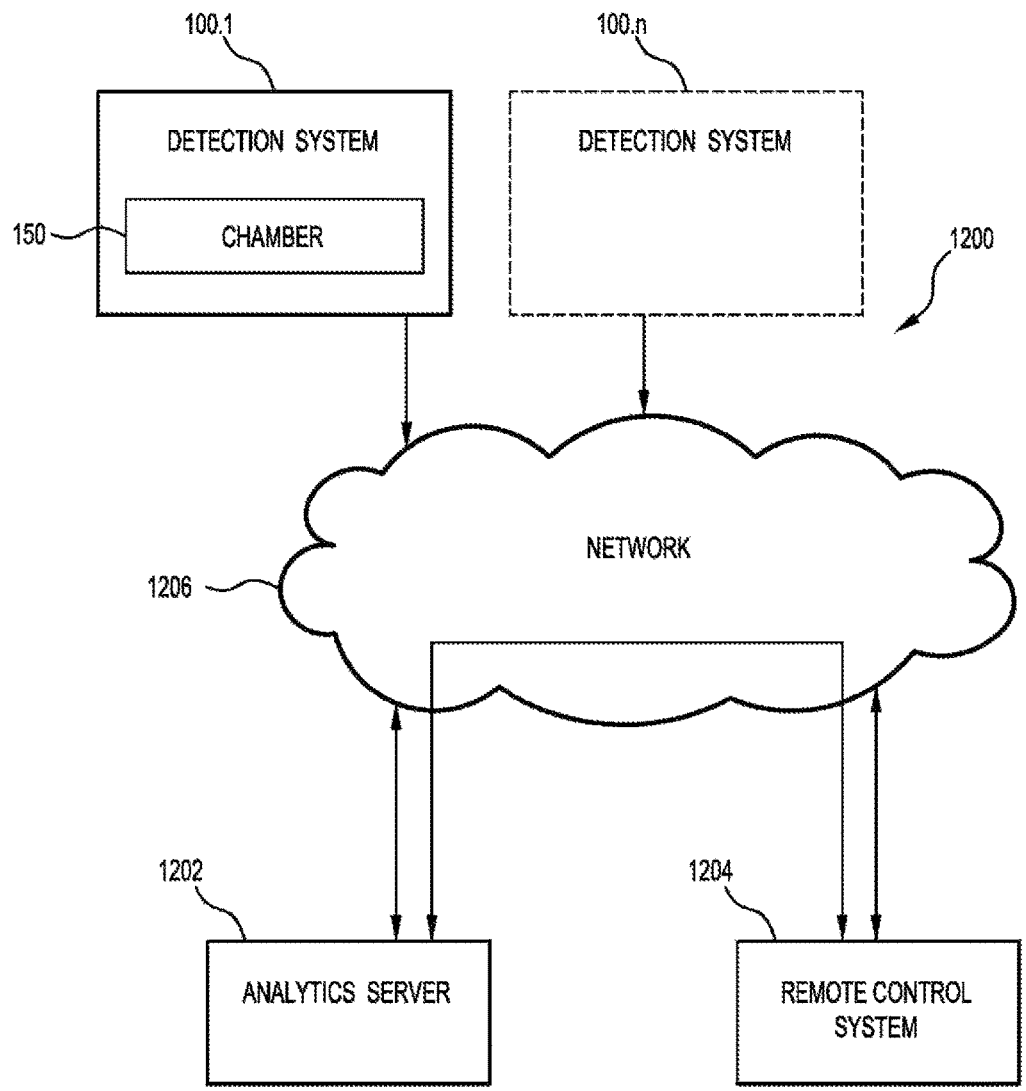
FIG. 12 illustrates a system architecture for providing smoke analytics functionality in one embodiment.

FIG. 12 is a system diagram illustrating one exemplary system employing a remote server to perform such analysis. In this embodiment the software for performing analysis necessary to extract information about particle type can be run on an external data processing system, e.g. a remote server 1202 or the like. The server system 1202 receives, inter alia, scattering data representing scattered light received by the particle detection system and generates an output representing a level of particles detected from one or more source by the particle detection system, using a method substantially as described in connection with FIG. 10. The server 1202 can be connected via a network 1206 to a plurality of detection systems 100.1 to 100.n. Such systems can be of the type illustrated in FIG. 1 and include a respective detection chamber 150.1 to 150.n for analysing samples for particles in the manner described above. The detector 102 of the system 100 is connected to the analytics server 1202 via any type of network 1206, e.g. a wired or wireless network or a combination thereof. The connect may be via the internet or any combination of private and/or public networks. Preferably the connection is a TCP connection.

Using this connection a detection system 1206.1 provides the server 1206 with the raw chamber data 1300 discussed above in connection with FIG. 11. The server in turn generates output date 1318 and transmits this via the network to its determined destination. For example the output to be displayed can be transmitted to a control system associated with the corresponding particle detection system 1202.1 The control system 1304 is preferably computing system running software configured to enable it to configure, commission and/or maintain a detection system 1202.1 (or a network of such systems). For example the remote control system can be a computer system running "VSC" system management software from Xtralis. The control system 1204 receives outputs from the server 1206 to enable it to generate a user interface communicating the analytics output to a user. In a preferred form the control system 1204 generates a graphical user interface including an element as described in connection with FIG. 11.

Advantageously a system architecture that separates smoke analytics and reporting, performed in this embodiment by the analytics server 1202 and control system 1204, from the underlying particle detection system enables the analytics and notification system to operate substantially independently from the usual detector alarms and pre-alarms. In this way the standards-approvals of the underlying detection system installed at the site being protected is minimally affected (or not affected at all), and there is minimum risk of affecting any critical functions of the detector. Moreover it facilitates the ability to upload new or improved analytics algorithms for use by multiple detectors without having to push updated software or analytics algorithms to each detector.

As will be appreciated some or all of the data processing system that implements the analytics functionality described above could be performed within the detector 1202.1, either by the main detector control system or on dedicated hardware (so as to minimise interaction with other functionality). Alternatively, the data processing system that performs the analytics functionality can be provided by a separate hardware module fitted to the detector. This advantageously allows the functionality to be retrofitted to previously installed systems which possess suitable particle detection systems, but unsuitable data processing systems.

In a further embodiment the data processing system providing the functions of the analytics server 1202 can be combined with the control system 1204. In such an example a central monitoring facility that controls a plurality of detectors at a site or across multiple sites can perform particle type and threat analytics for a plurality of connected particle detection systems. This may advantageously allow a coordinated response to detected fires or other events.

Figure 13:
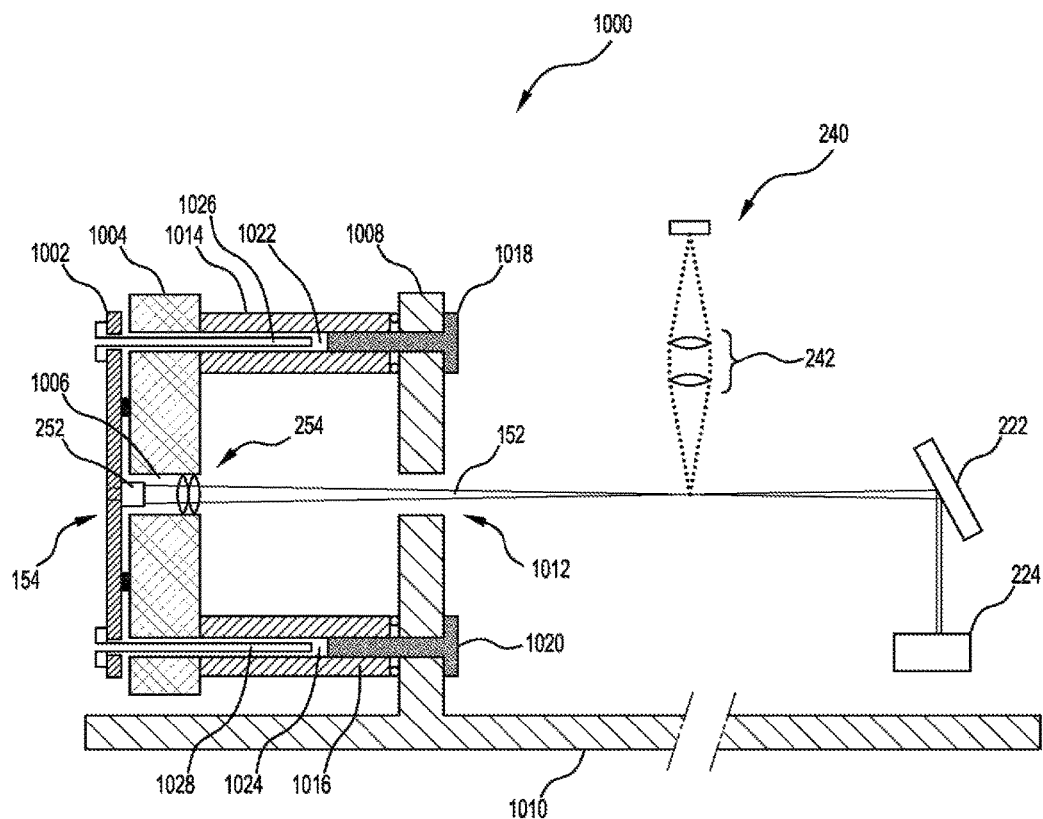
FIG. 13 is a cross-section through a mounting mechanism used for mounting a radiation source in some embodiments of the present invention, which illustrates a mechanism for steering the beam.

As noted above, in some embodiments of the particle detector and method the beam 152 converges to a waist 204 which is intended to be aligned with the focus of the optical system 242 of the imaging system 240 such that focussed images of the waist in the beam can be reliably captured. Thus, it is necessary to accurately position and align the beam with respect to this focal point. FIG. 13 illustrates a beam mounting and steering mechanism 1000 which may be used for this purpose, or more generally for steering a beam in an optical system. FIG. 13 illustrates a cross sectional view through the mounting arrangement 1000 of the radiation source 154 of the particle detector 102. Beginning with the radiation source 154 which in this case is a laser diode 252 mounted to a circuit board substrate 1002. The circuit board substrate 1002 is mounted to a mounting plate 1004 and together act as a carrier that provides mechanical support to the radiation source. The mounting plate also provides a structure (preferably aluminium or other metal) by which heat is dissipated from the laser diode 252. The mounting plate 1004 has an aperture 1006 formed through it in line with the laser diode 252 such that the beam 152 can propagate through the mounting plate 1004. Also mounted to the mounting plate 1004 are an optical system 254 comprising one or more lenses focus the beam 152. The mounting plate 1004 is connected to a support structure 1008 which is connected with or formed integrally with the chassis 1010 or housing 1010 of the detection chamber 150. The support structure 1008 also has a hole or cut-out 1012 formed therein for allowing the beam 152 to propagate past the support structure 1008. The mounting plate 1004 is mounted to the support structure 1008 via one, or preferably a plurality of members in the form of support posts 1014 and 1016 which are held by screws 118 and 120 respectively to the support structure of 1008. At least one of the support posts 1014 or 1016 has a heater associated with it and arranged to heat the support post. In this example, the posts are hollow and have a void 1022 and 1024 formed in their interior. The voids 1022 and 1024 contain a heater in the form of a resistor 1026 and 1028 which is electrically connected to the PCB 1002 and which protrudes through the support member 1004 into it. In a preferred embodiment the support posts are made from either plastic or nylon material (or other material which can be deformed, e.g. expanded, by the application of heat) so that by activating one or more of the heaters 1026 or 1028, thermal expansion of the posts 1014 or 1016 can be used to steer the beam. As will be appreciated, by differentially heating the two posts 1014 or 1016 the beam can be steered such that its focus coincides substantially the focus of the optical system 242.

Fore and aft movement of the focal point of the beam 152 may additionally be achieved by heating all of the support posts 1014 and 1016 such that the mounting plate 1014 is pushed away from the focal point of the optical system 224 thus moving the focus of the beam 152. Feedback for the beam steering mechanism 1000 is performed by measuring a received radiation level after the beam has traversed the region of interest in the chamber.

The radiation output level of the radiation source 252 can be locally monitored at the radiation source 154 end of the mounting arrangement eg. by a photodiode built into the radiation source 154 itself. The received radiation level at the other end of the chamber is monitored by use of a radiation sensor 224. The level of radiation falling on the radiation sensor 224 will vary according to the angle of alignment of the beam and thus can be used to determine the accuracy of alignment of the beam 152. In a preferred embodiment, the beam is not shone directly onto the radiation sensor 224 as this is likely to cause the radiation sensor 224 to saturate. In order to avoid this, the beam 152 is first directed onto a reflector 222. The reflector 222 absorbs a substantial proportion of incident radiation and reflects the remaining radiation onto the sensor 224 which can thus manifest beam alignment without saturation. In a preferred form the reflector 222 is made of a shiny black material reflecting about 1% of incident radiation and absorbing the rest.

As will be appreciated, by controlling activation of the heaters 1026 and 1028 the beam 152 position can be controlled to maintain constant radiation level at the radiation sensor 224 thereby controlling the position of the beam's focal point 204.

In some embodiments a particular beam modulation technique can be used to maximise the lifetime of the radiation emitter 252, which may be particularly useful when a UV or Violet radiation emitter is used. In one form, the emitter can be on/off modulated in a predetermined pattern to set the duty cycle of the emitter 252 such that a predetermined operational life can be expected. Rather than applying a regular and even on-off modulation that represents a low duty cycle, the inventors have determined that a specific modulation pattern can be selected that both extends emitter lifetime and provides acceptable detection performance, particularly for small particles.

In this regard, some embodiments use a modulation scheme that has a first number of first pulses of a first duration. The first pulses are at a relatively high power level. The modulation pattern also includes a second number of second pulses of second duration. The second pulses are at a second, lower power level. In one implementation, the first number of pulses is smaller than the second number of pulses such that fewer higher power pulses are made compared to the more frequent low power pulses. The first and second pulses may be interspersed with each other or grouped arranged into blocks of multiple pulses of the same type.

The following table gives one example of such a modulation scheme.

| Pulse type | Pulse duration | Pulse power | Number of pulses per second | Total duty cycle contribution |
|---|---|---|---|---|
| First | 5 ms | 100% | 5 | 2.5% |
| Second | 5 ms | 1% | 100 | 0.5% |

This scheme gives a 3% total duty cycle.

Advantageously, the high power pulses in the first periods provide enough radiation to enable in detection of low concentrations of small particles, which may be important for detecting certain types of fires at an early stage. The second pulses still provide sufficient radiation to enable detection of larger particles.

In other embodiments the modulation scheme can employ a first number of first pulses of a first duration. The first pulses are at a relatively high power level. The modulation pattern also includes a second number of second pulses of second duration. The second pulses are at a second, lower power level. The modulation pattern also includes a third number of third pulses of third duration. The third pulses are at a third, yet lower power level. Reduced power pulses may be achieved by lowering the drive to the light emitter or by switching the emitter on and off at a higher frequency within the pulse duration (pulse-width modulation) or by a combination of the two.

In a most preferred form, the higher power pulses are fewer in number and in overall duration compared to the low power pulses. The first, second and subsequent pulses may be interspersed with each other or grouped arranged into blocks of multiple pulses of the same type.

The following table gives one example of such a modulation scheme.

| Pulse Type | Pulse Duration (ms) | Pulse Power (%) | Number of pulses per second | Total duty cycle contribution (%) |
|---|---|---|---|---|
| First | 20 | 100 | 1 | 2 |
| Second | 50 | 10 | 2 | 1 |
| Third | 50 | 2 | 5 | 0.5 |

This scheme gives a 3.5% total duty cycle. Advantageously, the high power pulses in the first periods provide enough light to enable detection of low concentrations of small particles, which may be important for detecting certain types of fires at an early stage. The second pulses provide sufficient light intensity to enable detection of particles which are larger in size, without causing saturation of the electronic light sensor, while their extended duration also improves the probability of detection of the larger particles, which are generally present less frequently than the smaller particles. Subsequent lower power pulses enable detection of even larger particles and are less frequently occurring.

As will be appreciated, this modulation pattern can be changed to other levels to those described herein to obtain a chosen balance between particle detection sensitivity and emitter lifetime.

In a further aspect there is provided a particle detector that changes at least one light scattering characteristic of particles entrained in a sample flow being analysed by application of heat. In one embodiment the particle detector includes a heating element in a flow path configured to heat the sample flow.

In some embodiments heating can be performed at a sufficient rate to drive off water adsorbed or absorbed by particles or otherwise bound to particles thereby changing the optical properties of the particles prior to analysis.

In other embodiments heating can be performed at a sufficient rate to burn unburned particles thereby changing the optical properties of the particles prior to analysis.

The heating element is preferably a resistive element connected to a power source. Most preferably the heating element can be selectively activated, to enable selective heating of the sample flow. Activation of the heating element may be performed continuously, intermittently or in response to a pre-determined particle detection event. The predetermined particle detection event may be the detection of particles at a predetermined level or having a predetermined particle size distribution as discussed above.

In a further aspect there is provided a method in a particle detection system comprising:
(a) receiving a sample flow from a region being monitored,
(b) heating the sample flow to change the optical properties of at least some particles entrained in the sample flow;
(c) analysing the sample flow to detect particles.

Step (b) can be performed intermittently, either at random times or periodically.

Step (b) can be performed in response to the occurrence of a predetermined event. Accordingly the method can include determining the occurrence of a predetermined event and initiating step (b).

The predetermined event can include any one or more of:
The detection of particles having a predetermined size distribution;
The detection of particles at a predetermined concentration;
Detecting particles for a predetermined duration.

The method can further include:
(d) ceasing heating the sample flow;
(e) analysing the sample flow.

The method can include comparing the result of the analysis of steps (c) and (e) to determine a property of the particles entrained in the sample flow. The property can include any one or more of:
a particle size distribution of the particles;
a type of particles;
a cause of the emission of the particles.

Figure 14:
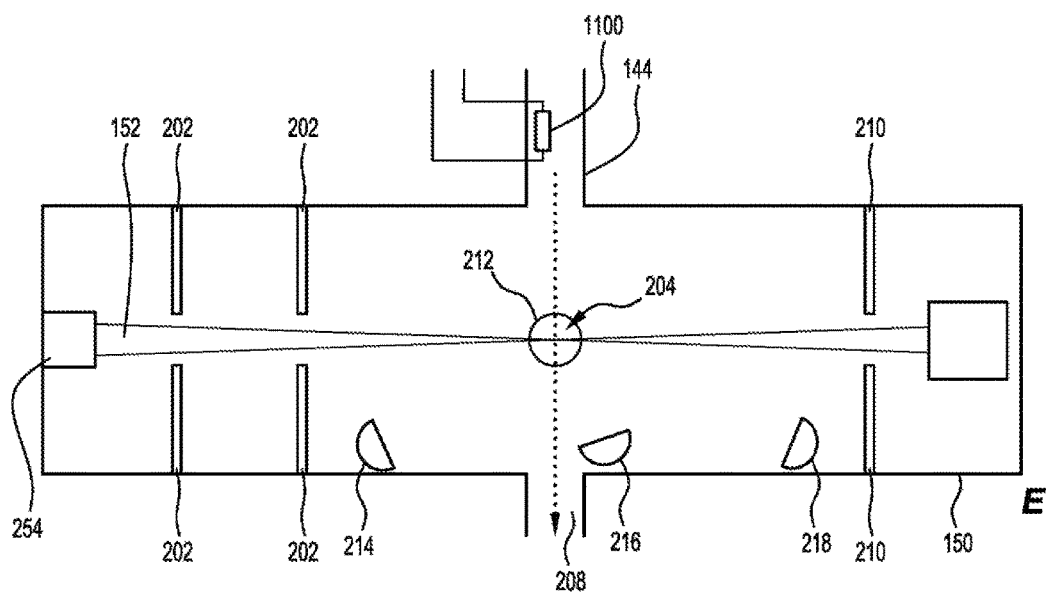
FIG. 14 illustrates an embodiment of the present invention including a heater used to heat the sample flow prior to analysis.

FIG. 14 illustrates a schematic view of a detection chamber 150, which is substantially identical to that of FIGS. 2A and 2B. However, in this embodiment the sample inlet 144 includes a heater element 1100. The heater element 1100 is a resistive heater and is exposed to the sample flow as it passes along the inlet 144 towards the detection chamber 150. The heater element 144 can be selectively activated by the system controller to heat the sample flow when required. In use, the heater is activated to aid in making a determination of the type of particles entrained in the sample flow.

Figure 15:
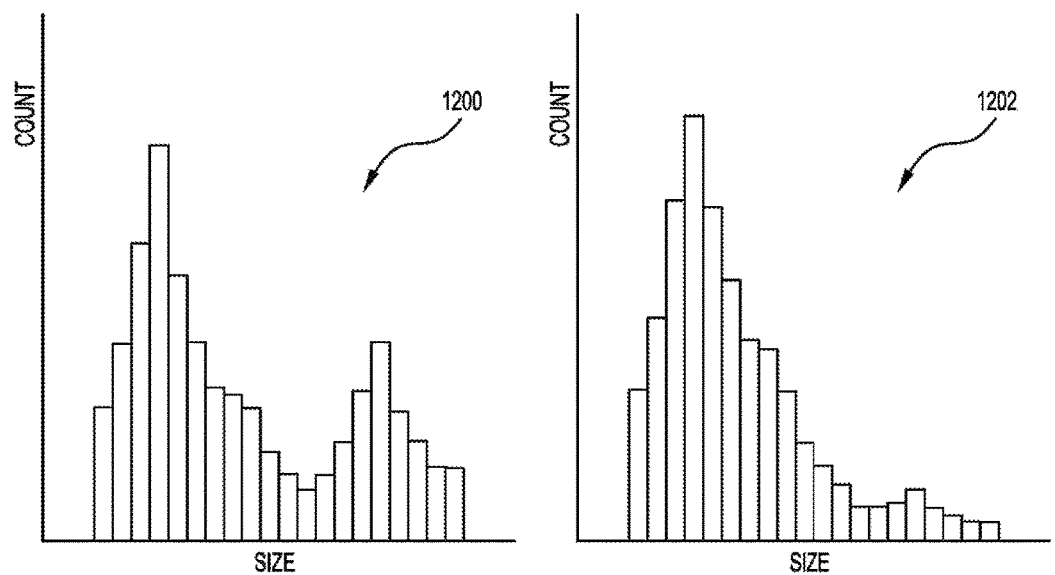
FIG. 15 illustrates a histogram of the count of particles of different sizes before and after heating the sample flow.

FIG. 15 illustrates a particle size distribution histogram showing the number of particles detection in a range of particle size bins. The histogram shows two size distributions, the white distribution 1200 illustrates the particle size distribution detected without the heater 1100 activated, and the shaded distribution 1202 illustrates the particle size distribution detected with the heater 1100 activated. When the heater is inactive (white distribution) the histogram has a large number of large sized particles, This can indicate several conditions, such as:
1. The particles being detected are caused by a certain substance, or the burning of a substance, which produces a characteristic particle size distribution as detected.
2. A bi-modal distribution of particle sizes has been detected indicating a mixture of two particle types, or cause of particles are present.
3. Some particles being detected have water bound to them and thus have their size over estimated because of the added water.
4. The sample flow contains large unburned particles in the sample flow.

If, when the heater is activated, the size distribution changes, say to have the shaded particle size distribution, this suggests that either condition 3 or 4 is causing the particle size distribution. For example heating the sample flow at a first level will drive the water off the particles and they are detected as their normal (i.e. de-watered) size. This can cause the number of small particles to increase and large particle count to decrease thus indicating the cause of the detection of a large number of relatively large particles. Such an embodiment may be particularly useful in humid environments where water droplets are common.

On the other hand if heating the sample flow to a high temperature, (i.e. to a level that some unburned particles are burned), the number of small particles detected may rise. This indicates that the sample flow contains large unburned particles that are being decomposed in the burning process. This change can give a key indication as to the nature of the particles being detected or the event that has caused them.

In smoke detection scenarios, it may be that the fire causing the smoke develops over time and the particle size distribution changes over time. By repeating the process or activating and deactivating the heater or setting the heater to different heat levels the development of the particle size distribution can be more reliably detected.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A particle detector configured to detect the presence of airborne particles entrained in an air sample, the particle detector including:
   a detection chamber for receiving a sample flow comprising an air sample for analysis;
   a radiation source configured to emit a beam of radiation having known polarization characteristics, said beam propagating across at least part of the chamber and being arranged to traverse the sample flow at a region of interest;
   an arrangement of radiation receivers configured to receive radiation that is scattered from the beam by interaction with particles entrained in the sample flow and to generate at least one output signal representing the received radiation, said arrangement of radiation receivers including a plurality of receivers arranged with respect to the beam and region of interest such that the arrangement of radiation receivers is configured to receive radiation at a plurality of scattering angles and in a plurality of polarization angles with respect to a direction of propagation and known polarization of the beam;
   an image sensor having a plurality of pixels and being configured to capture images of the region of interest by receiving radiation scattered out of the beams; and
   a controller configured to analyze the at least one output signal from the radiation receiver representing the received radiation and to analyze the images to determine the presence of airborne particles entrained in the sample flow interacting with the beam in the region of interest based on scattered radiation contained in the captured images to determine the presence of airborne particles entrained in the sample flow.

2. The particle detector as claimed in claim 1 wherein the arrangement of radiation receivers includes a plurality of radiation receiving sensors each configured to receive radiation at a respective scattering angle.

3. The particle detector as claimed in claim 2 wherein each sensor is arranged to receive radiation at a known polarization angle relative to an angle of polarization to the beam.

4. The particle detector as claimed in claim 2 wherein the detector is configured to temporally correlate the output signals from at least a subset of the sensors.

5. The particle detector as claimed in claim 4 wherein the temporally correlated output signals are used to identify an interaction between a particle of interest and the beam.

6. The particle detector as claimed in claim 4 wherein the temporally correlated output signals are used to determine a particle characteristic.

7. The particle detector as claimed in claim 1 wherein the arrangement of radiation receivers includes a first plurality of radiation receiving sensors configured to receive radiation a first polarization angle relative to the beam, wherein each of said first plurality of radiation sensors are arranged to receive at a respective scattering angle.

8. The particle detector as claimed in claim 7 wherein the arrangement of radiation receivers includes a second plurality of radiation receiving sensors configured to receive radiation at a second polarization angle, that is different to the first polarization angle, relative to the beam, wherein said second plurality of radiation sensors are each arranged to receive radiation at a respective scattering angle.

9. The particle detector as claimed in claim 8 wherein the first and second plurality of radiation sensors are arranged such that at least one of the sensors of each of the first and second plurality of radiation sensors are arranged to receive radiation at the same respective scattering angle.

10. The particle detector as claimed in claim 1 wherein the radiation source emits a beam of radiation having a wavelength that is sufficiently short to be scattered from air in the detection chamber to a sufficient extent that an image of the beam can be captured by the image sensor without any particles being entrained in a sample flow.

11. The particle detector as claimed in claim 10 wherein the beam is in the violet or ultraviolet region of the electromagnetic spectrum.

12. The particle detector as claimed in claim 1 wherein controller is configured to perform background cancellation on captured images.

13. The particle detector as claimed in claim 12 wherein background cancellation involves correcting received radiation levels within an integration region of the image that includes the beam on the basis of a representative, received background radiation level that has been determined from at least one region of the image not including the beam.

14. The particle detector as claimed in claim 12 wherein background cancellation is performed in a piecewise fashion along the integration region using corresponding piecewise defined background cancellation regions.

15. The particle detector as claimed in claim 1 wherein the controller is configured to analyze the images to determine the presence of a particle by identifying a peak in received radiation intensity in the image of the integration region.

16. The particle detector as claimed in claim 15 wherein, in the event that the peak is above a threshold level a particle can be determined to have interacted with the beam and thus detected.

17. The particle detector as claimed in claim 16 wherein the threshold represents any one of the following properties of the peak:
   maximum received intensity;
   or total received energy in the peak.

18. The particle detector as claimed in claim 1 wherein the particle detector includes a detection chamber and radiation source emitting a single beam of radiation, wherein the arrangement, of radiation receivers and image sensor are arranged to receive radiation from a common region of interest.

19. The particle detector as claimed in claim 18 wherein the controller correlates the output of the image sensor and arrangement of radiation receivers.

20. A particle detector including:
   a detection chamber for receiving a sample flow comprising an air sample for analysis;
   a radiation source configured to emit a beam of radiation, said beam propagating across at least part of the chamber and being arranged to traverse the sample flow at a region of interest;
   an arrangement of radiation receivers configured to receive radiation that is scattered from the beam by interaction with particles entrained in the sample flow and generate at least one output signal representing the received radiation, said arrangement of radiation receivers including an image sensor having a plurality of pixels and being configured to capture images of the region of interest by receiving radiation scattered out of the beam, and at least one other radiation receiver, and a controller configured to analyze the at least one output signal representing the received radiation to determine the presence of airborne particles entrained in the sample flow.

21. The particle detector as claimed in claim 20 wherein the arrangement of radiation receivers is configured to receive radiation at a plurality of scattering angles and in a plurality of polarization angles with respect to a direction of propagation and known polarization of the beam.

22. The particle detector as claimed in claim 21 wherein the arrangement of radiation receivers includes a plurality of radiation receiving sensors each configured to receive radiation at a respective scattering angle.

23. The particle detector as claimed in claim 20 wherein the radiation source includes an optical system to focus the beam.

24. The particle detector as claimed in claim 20 wherein the beam is focused so that it converges towards the region of interest.

25. The particle detector as claimed in claim 20 wherein one or more of, sample flow rate; beam cross section; beam shape; or beam alignment relative to the sensors comprising the radiation sensing system; are selected or controlled, such that for a predetermined concentration of particles in the sample flow, on average, interactions between particles entrained in the sample and the beam that scatter radiation in a manner that may be received directly by a sensor of the radiation sensing system, are non-overlapping in time.

26. The particle detector as claimed in claim 20 wherein the detector is configured, for each particle of interest detected, to determine a particle size or total brightness.

27. The particle detector as claimed in claim 20 wherein the particle detector is a smoke detector.

* * * * *